(12) United States Patent
Kim et al.

(10) Patent No.: US 7,534,807 B2
(45) Date of Patent: May 19, 2009

(54) DE NOVO SYNTHESIS OF BACTERIOCHLORINS

(75) Inventors: Han-Je Kim, Raleigh, NC (US); Jonathan S. Lindsey, Raleigh, NC (US)

(73) Assignee: North Carolina State University, Raleigh, NC (US)

(*) Notice: Subject to any disclaimer, the term of this patent is extended or adjusted under 35 U.S.C. 154(b) by 34 days.

(21) Appl. No.: 11/357,833

(22) Filed: Feb. 17, 2006

(65) Prior Publication Data

US 2006/0194960 A1   Aug. 31, 2006

Related U.S. Application Data

(60) Provisional application No. 60/720,175, filed on Sep. 23, 2005, provisional application No. 60/654,270, filed on Feb. 18, 2005.

(51) Int. Cl.
*A61K 31/40* (2006.01)
*A01N 43/38* (2006.01)

(52) U.S. Cl. .................................................... 514/410
(58) Field of Classification Search .................. None
See application file for complete search history.

(56) References Cited

U.S. PATENT DOCUMENTS

| | | | |
|---|---|---|---|
| 5,064,952 A | 11/1991 | Chang et al. |
| 5,171,741 A | 12/1992 | Dougherty |
| 5,173,504 A | 12/1992 | Dougherty |
| 5,330,741 A | 7/1994 | Smith et al. |
| 6,376,483 B1 | 4/2002 | Robinson |
| 6,407,330 B1 | 6/2002 | Lindsey et al. |
| 6,420,648 B1 | 7/2002 | Lindsey |
| 6,596,935 B2 | 7/2003 | Lindsey et al. |
| 6,603,070 B2 | 8/2003 | Lindsey et al. |
| 6,765,092 B2 | 7/2004 | Lindsey et al. |
| 6,794,505 B1 | 9/2004 | Robinson et al. |
| 6,827,926 B2 | 12/2004 | Robinson et al. |
| 6,828,439 B1 | 12/2004 | Zaleski et al. |
| 6,849,730 B2 | 2/2005 | Lindsey et al. |
| 6,916,982 B2 | 7/2005 | Loewe et al. |
| 6,924,375 B2 | 8/2005 | Lindsey et al. |
| 6,946,552 B2 | 9/2005 | Lindsey et al. |
| 7,022,862 B2 | 4/2006 | Lindsey et al. |
| 7,148,361 B2 | 12/2006 | Lindsey et al. |
| 7,282,582 B2 | 10/2007 | Lindsey et al. |
| 7,317,108 B2 | 1/2008 | Lindsey et al. |
| 7,323,561 B2 | 1/2008 | Lindsey et al. |
| 7,332,599 B2 | 2/2008 | Yu et al. |
| 7,378,520 B2 | 5/2008 | Lindsey et al. |
| 7,423,160 B2 | 9/2008 | Lindsey et al. |
| 2002/0185173 A1 | 12/2002 | Lindsey et al. |
| 2003/0075216 A1 | 4/2003 | Loewe et al. |
| 2003/0096978 A1 | 5/2003 | Lindsey et al. |
| 2003/0111108 A1 | 6/2003 | Lindsey et al. |
| 2004/0044197 A1 | 3/2004 | Pandey et al. |
| 2004/0186285 A1 | 9/2004 | Nifantiev et al. |
| 2004/0244831 A1 | 12/2004 | Lindsey |
| 2004/0259810 A1 | 12/2004 | Grierson et al. |
| 2005/0277770 A1 | 12/2005 | Balakumar et al. |
| 2006/0009638 A1 | 1/2006 | Lindsey et al. |

OTHER PUBLICATIONS

Dorwald F. A. Side Reactions in Organic Synthesis, 2005, Wiley: VCH, Weinheim p. IX of Preface.*
International Search Report and Written Opinion for PCXT/US06/05658; date of mailing Nov. 7, 2006.
Sternberg et al. "Porphyrin-based Photosensitizers for Use in Photodynamic Therapy" *Tetrahedron 54*: 4151-4202 (1998).
Prinsep M R et al. Further tolyporphins from the blue-green alga *Tolypothrix nodosa*. Tetrahedron (1995), vol. 51, No. 38, pp. 10523-10530.
Wang W and Kishi Y. Synthesis and structure of tolyporphin A O,O-Diacetate. Organic Letters (1999), vol. 1, No. 7, pp. 1129-1132.
Jacobi P A et al. A new synthesis of chlorins. Organic Letters (2001), vol. 3, No. 6, pp. 831-834.
Kim H-J and Lindsey J S. De novo synthesis of stable tetrahydroporphyrinic macrocycles: bacteriochlorins and a tetradehydrocorrin. The Journal of Organic Chemistry (2005), vol. 70, No. 14, pp. 5475-5486.
Smith J and March J. Chapter 19: Reactions. March's Advanced Organic Chemistry: Reactions, Mechanisms, and Structure, 5th Ed., (2001), pp. 1531-1533. John Wiley & Sons, Inc. New York, NY.
Taniguchi M et al. Synthesis and electronic properties of regioisomerically pure oxochlorins. J. Org. Chem. (2002), vol. 67, pp. 7329-7342.

* cited by examiner

*Primary Examiner*—James O Wilson
*Assistant Examiner*—Jeffrey H Murray
(74) *Attorney, Agent, or Firm*—Myers Bigel Sibley & Sajovec, P.A.

(57) ABSTRACT

A method of making a bacteriochlorin is carried out by condensing a pair of compounds of Formula II

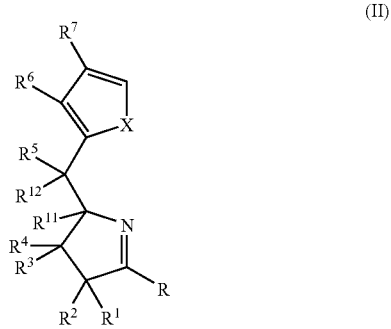

(II)

to produce the bacteriochlorin, wherein R is an acetal or aldehyde group. The condensing may be carried out in an organic solvent, preferably in the presence of an acid. The bacteriochlorins are useful for a variety of purposes such as active agents in photodynamic therapy, luminescent compounds in flow cytometry, solar cells, light harvesting arrays, and molecular memory devices.

6 Claims, 4 Drawing Sheets

DE NOVO SYNTHESIS OF BACTERIOCHLORINS

RELATED APPLICATIONS

This application claims the benefit of U.S. Provisional Applications Ser. Nos. 60/654,270, filed Feb. 18, 2005, and 60/720,175, filed Sep. 23, 2005, the disclosures of which are incorporated by reference herein in their entirety.

This invention was made with US Government support under Grant Number GM36238 from the National Institutes of Health. The US Government has certain rights to this invention.

FIELD OF THE INVENTION

The present invention concerns bacteriochlorins, methods and intermediates for the synthesis of bacteriochlorins, and methods of using such bacteriochlorins for, among other things, diagnostic and therapeutic purposes such as photodynamic therapy (PDT), as luminescent compounds in flow cytometry, in solar cells, in light harvesting arrays, and in molecular memory devices.

BACKGROUND OF THE INVENTION

The progressive $2e^-/2H^+$ reduction of the porphyrinic macrocycle along the series porphyrin, chlorin (a dihydroporphyrin) and bacteriochlorin (a tetrahydroporphyrin) causes profound changes in chemical and physical properties (Scheme 1). The reduction alters the symmetry yet each macrocycle maintains an 18 π-electron conjugated system as required for aromaticity. One striking change upon reduction is the large increase in absorption in the red or near-IR region of the spectrum.

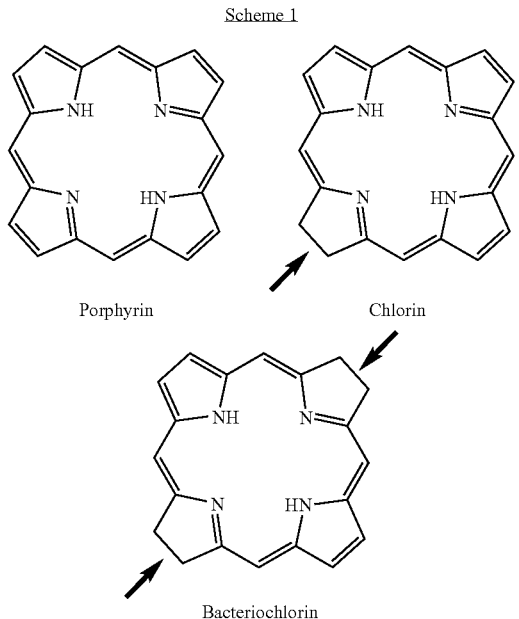

Scheme 1

Porphyrin    Chlorin

Bacteriochlorin

The changes in physical properties have been famously exploited by biological systems; the chlorin macrocycle provides the basis for chlorophyll a and b in plant photosynthesis while the bacteriochlorin macrocycle provides the basis for bacteriochlorophyll a in bacterial photosynthesis. The striking change in absorption is illustrated for a representative porphyrin, chlorin, and bacteriochlorin in FIG. 1. (Sternberg, E. D.; Dolphin, D. *Tetrahedron* 1998, 54, 4151-4202)

Two distinct types of bacteriochlorins occur in Nature, bacteriochlorophylls (type a, b, or g) and tolyporphins (A-J). The bacteriochlorophylls serve as the principal light-absorbing pigments and energy/electron-transfer components in bacterial photosynthetic systems. Bacteriochlorophyll a is the most widely distributed bacteriochlorin pigment and was the first bacteriochlorophyll isolated as a pure compound (Scheer, H. In *The Porphyrins*; Dolphin, D., Ed.; Academic Press: New York, 1978; Vol. I, p 31; Scheer, H.; Inhoffen, H. H. In *The Porphyrins*; Dolphin, D., Ed.; Academic Press: New York, 1978; Vol. I, p 45). Tolyporphin A, a non-photosynthetic bacteriochlorin pigment, was isolated from the cyanophyte microalga *Tolypothrix nodosa* in 1992, and a number of additional tolyporphins that contain the bacteriochlorin system have since been isolated (Prinsep, M. R. et al., *J. Am. Chem. Soc.* 1992, 114, 385-387; Prinsep, M. R. et al., *Tetrahedron* 1995, 51, 10523-10530; Prinsep, M. R. et al., *J. Nat. Prod.* 1998, 61, 1133-1136). The structures of bacteriochlorophyll a and tolyporphin A are shown in Scheme II.

Scheme II

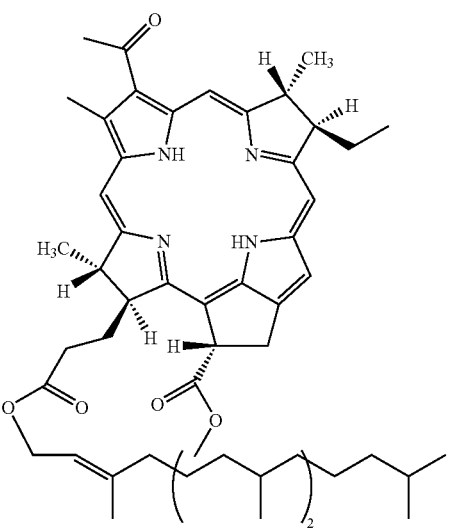

Bacteriochlorophyll a

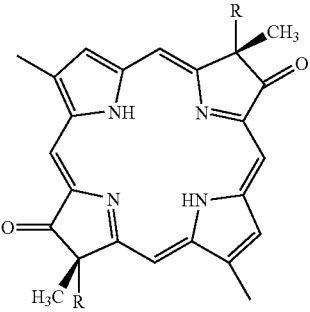

Tolyporphin A

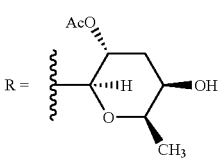

Surprisingly few methods exist for the preparation of bacteriochlorins despite the importance of this class of compounds (Johnson, A. W.; Oldfield, D. *J. Chem. Soc.* 1965, 4303-4312; Dinello, R. K.; Dolphin, D. *J. Org. Chem.* 1980, 45, 5196-5204; Chang, C. K.; Sotriou, C. *J. Org. Chem.* 1987, 52, 926-929; Kozyrev, A. N. et al., *Tetrahedron Lett.* 1996, 37, 3781-3784; Shea, K. M. et al., *Tetrahedron* 2000, 56, 3139-3144). With regard to the naturally occurring bacteriochlorins, the total synthesis of the O,O-diacetate of tolyporphin A was reported several years ago by Kishi, entailing >20 steps and affording <5 mg of product (Wang, W.; Kishi, Y. *Org. Lett.* 1999, 1, 1129-1132). To our knowledge, no total syntheses of bacteriochlorophyll a have been reported. A chief obstacle to handling bacteriochlorophyll a is its pronounced tendency to undergo dehydrogenation to give the corresponding chlorin. The same tendency for oxidative reversion to the chlorin or porphyrin occurs with bacteriochlorins that have been prepared by hydrogenation of the porphyrin or chlorin (Dorough, G. D.; Miller, J. R. *J. Am. Chem. Soc.* 1952, 74, 6106-6108; Whitlock, H. W. et al., *J. Am. Chem. Soc.* 1969, 91, 7485-7489; Fajer, J. et al., *Proc. Nat. Acad. Sci. USA.* 1974, 71, 994-998; Bonnett, R. et al., *Biochem. J.* 1989, 261, 277-280; Grahn, M. F. et al., *J. Photochem. Photobiol. B: Biol.* 1997, 37, 261-266; Senge, M. O. et al., S. *Tetrahedron* 1998, 54, 3781-3798). More resilient bacteriochlorins have been prepared by derivatization of porphyrins or chlorins via vicinal dihydroxylation (typically followed by pinacol rearrangement for porphyrins that bear β-substituents) (Chang, C. K. et al., *J. Chem. Soc. Chem. Commun.* 1986, 1213-1215; Adams, K. R. et al., *J. Chem. Soc. Perkin Trans.* 1 1992, 1465-1470; Pandey, R. K. et al., *Tetrahedron* 1992, 51, 7815-7818; Kozyrev, A. N. et al., *Tetrahedron Lett.* 1996, 37, 3781-3784; Pandey, R. K. et al., *J. Med. Chem.* 1997, 40, 2770-2779; Pandey, R. K. et al., *J. Org Chem.* 1997, 62, 1463-1472; Zheng, G. et al., *J. Org. Chem.* 1999, 64, 3751-3754; Chen, Y. et al., *J. Org. Chem.* 2001, 66, 3930-3939; Li, G. et al., *J. Org. Chem.* 2004, 68, 3762-3772), Diels-Alder reaction (Tomé, A. C. et al., *Chem. Commun.* 1997, 1199-1200; Vincente, M. G. H. et al., *Chem. Commun.* 1998, 2355-2356; Cavaleiro, J. A. S. et al., *J. Hetetocyclic Chem.* 2000, 37, 527-534), or 1,3-dipolar cycloaddition (Silva, A. M. G. et al., *Tetrahedron Lett.* 2002, 43, 603-605). While each of the derivatization methods has merit, a key limitation lies in the formation of regioisomers upon use of porphyrinic substrates bearing a distinct pattern of substituents. On the other hand, modification of naturally occurring bacteriochlorophylls can yield elaborate bacteriochlorin derivatives, but the presence of a nearly full complement of peripheral substituents in the naturally available starting materials restricts synthetic flexibility (Mironov, A. F et al., *J. Porphyrins Phthalocyanines* 2003, 7, 725-730; Mironov, A. F. et al., *Russ. J. Bioorg. Chem.* 2003, 29, 190-197; Hartwich, G. et al., *J. Am. Chem. Soc.* 1998, 120, 3675-3683; Tamiaki, H. et al., *Tetrahedron: Asymmetry* 1998, 9, 2101-2111; Wasielewski, M. R. et al., *J. Org. Chem.* 1980, 45, 1969-1974).

SUMMARY OF THE INVENTION

A first aspect of the present invention is a method of making a compound of Formula I:

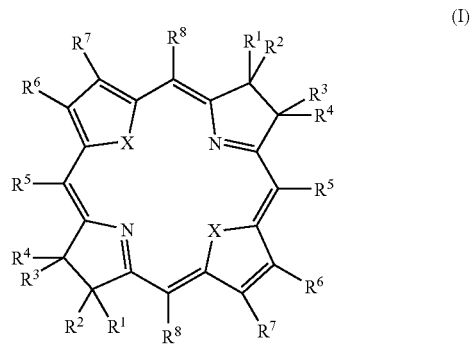

wherein:
X is selected from the group consisting of Se, NH, CH$_2$, O and S;
R$^1$, R$^2$, R$^3$, R$^4$, R$^5$, R$^6$, R$^7$ and R$^8$ is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, linking groups, and surface attachment groups;
or R$^1$ and R$^2$ together are =O or spiroalkyl;
or R$^3$ and R$^4$ together are =O or spiroalkyl;
and optionally but preferably subject to the proviso that (i) neither R$^1$ nor R$^2$ is H, or (ii) neither R$^3$ nor R$^4$ is H; and
R$^8$ is H, alkoxy or as given above;
the method comprising self-condensing a compound (or condensing a pair of compounds) of Formula II:

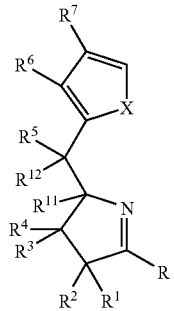

in an organic solvent in the presence of an acid to produce the compound of Formula I, wherein:
R is an acetal or aldehyde group;
X and R$^1$ to R$^7$ are as given above and R$^8$ is H (or alkoxy, or as otherwise contributed by the acetal or aldehyde group); and
R$^{11}$ and R$^{12}$ are each H; or R$^{11}$ and R$^{12}$ together form a covalent bond.
Optionally, the compound can then be further derivatized to exchange hydrogen at the R$^8$ position with the further substituents given above, in accordance with known techniques.

Compounds of the present invention (sometimes referred to as "active compounds" herein) include compounds of Formula I, and pharmaceutically acceptable salts, prodrugs and conjugates thereof.

A further aspect of the invention is a method for treating a target in a subject in need thereof, comprising: (i) administering to the subject the active compound as described herein or a pharmaceutically acceptable conjugate thereof that preferentially associates with the target, and (ii) irradiating the target with light of a wavelength and intensity sufficient to treat the target. Suitable subjects include but are not limited to subjects afflicted with opportunistic infections, with burns (particularly burns that have become infected), sepsis, with ulcers, periodontal disease, atherosclerosis, cosmetic and dermatologic conditions, acne, infectious diseases, tissues that require sealing such as in wounds or surgical incisions, and subjects afflicted with neoplastic disease or cancer.

A further aspect of the invention is a photodynamic therapy method for treating hyperproliferative tissue in a subject in need thereof, comprising: (i) administering to the subject an active compound as described herein or a pharmaceutically acceptable conjugate thereof that preferentially associates with the hyperproliferative tissue, and (ii) irradiating the target with light of a wavelength and intensity sufficient to activate the compound, and thereby treat the hyperproliferative tissue.

A further aspect of the invention is a method for detecting the presence of a hyperproliferative tissue in a subject, comprising: (i) administering to the subject an active compound as described herein or a pharmaceutically acceptable conjugate thereof that preferentially associates with the hyperproliferative tissue; and then (ii) visualizing the compound within the patient.

A further aspect of the present invention is a kit to treat hyperproliferative disorders, comprising the active compound described herein or a pharmaceutically acceptable conjugate thereof and instructions teaching a method of photodynamic therapy.

A further aspect of the present invention is a kit to label specific tissues for diagnosis comprising the active compound described herein or a pharmaceutically acceptable conjugate thereof and instructions teaching a method of imaging (e.g., magnetic resonance imaging).

A further aspect of the present invention is, in a method of detecting particles such as cells by flow cytometry, where the particles are labelled with a detectable luminescent compound, the improvement comprising utilizing a bacteriochlorin as described herein as the luminescent compound.

The foregoing and other objects and aspects of the invention are explained in greater detail in the drawings herein and the specification set forth below.

Figure 1:
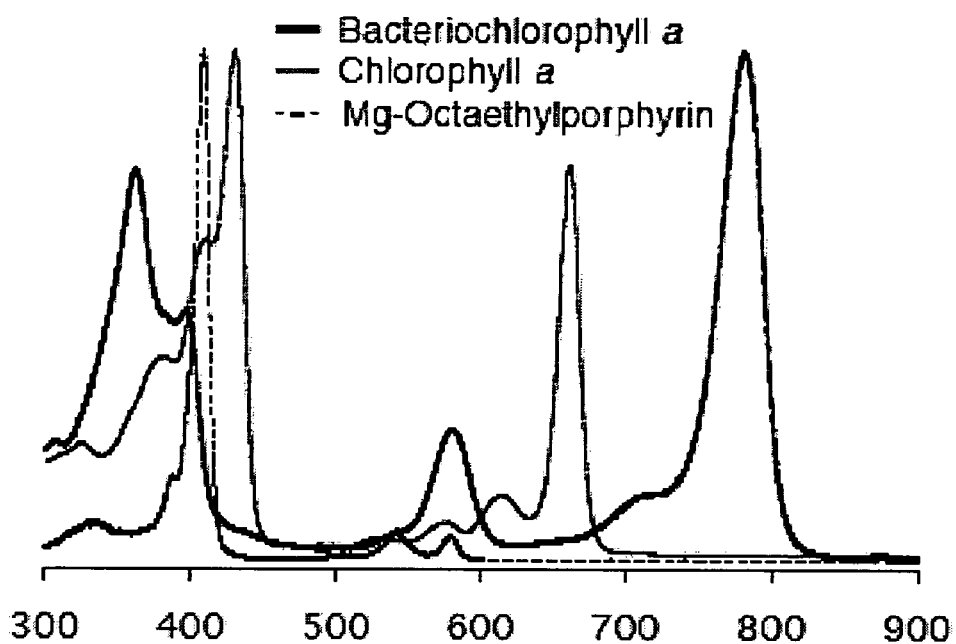
FIG. 1. Absorption spectra of Mg-octaethylporphyrin, chlorophyll α, and bacteriochlorophyll α. The molar absorption coefficients are $\epsilon_{409\ nm}$=408,300 (Zass, E. et al., *Helv. Chim. Acta* 1980, 63, 1048-1067), $\epsilon_{428.5\ nm}$=111,700 (Strain, H. H. et al., *Biochim. Biophys. Acta* 1963, 75, 306-311), and $\epsilon_{781\ nm}$=92,300 M$^{-1}$ cm$^{-1}$ (Connolly, J. S. et al., *Photochem. Photobiol.* 1982, 36, 565-574). The spectra are normalized for comparison purposes.

The present invention is explained in greater detail in the specification set forth below.

DETAILED DESCRIPTION OF THE PREFERRED EMBODIMENTS

"Acetal" as used herein refers to a group of the formula:

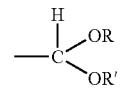

where R and R' are each suitable groups, e.g., groups independently selected from the group consisting of alkyl, aryl, alkylaryl, or where R and R' together form a group —R"— where R" is an alkylene (i.e., cycloalkyl). The acetal is preferably reasonably robust, and hence it is preferred that at least one, or more preferably both, of R and R' is not methyl, and it is particularly preferred that neither R nor R' is H.

"Aldehyde" as used herein refers to a group of the formula:

"Halo" as used herein refers to any suitable halogen, including —F, —Cl, —Br, and —I.

"Mercapto" as used herein refers to an —SH group.

"Azido" as used herein refers to an —N$_3$ group.

"Cyano" as used herein refers to a —CN group.

"Hydroxyl" as used herein refers to an —OH group.

"Nitro" as used herein refers to an —NO$_2$ group.

"Alkyl" as used herein alone or as part of another group, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "akyl" or "loweralkyl" is intended to include both substituted and unsubstituted alkyl or loweralkyl unless otherwise indicated and these groups may be substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl- S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkenyl" as used herein alone or as part of another group, refers to a straight or branched chain hydrocarbon containing from 1 to 10 carbon atoms (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkynyl" as used herein alone or as part of another group, refers to a straight or branched chain hydrocarbon containing from 1 to 10 carbon atoms (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralknynyl unless otherwise indicated and these groups may be substituted with the same groups as set forth in connection with alkyl and loweralkyl above.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Acyl" as used herein alone or as part of another group refers to a —C(O)R radical, where R is any suitable substituent such as aryl, alkyl, alkenyl, alkynyl, cycloalkyl or other suitable substituent as described herein.

"Haloalkyl" as used herein alone or as part of another group, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Amino" as used herein means the radical —NH$_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —NR$_a$R$_b$, where R$_a$ and R$_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —NR$_a$R$_b$, where R$_a$ is an acyl group as defined herein and R$_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Formyl" as used herein refers to a —C(O)H group.

"Carboxylic acid" as used herein refers to a —C(O)OH group.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Amide" as used herein alone or as part of another group refers to a —C(O)NR$_a$R$_b$ radical, where R$_a$ and R$_b$ are any suitable substituent such as alkyl, cycloalkyl, alkenyl, alkynyl or aryl.

"Sulfonamide" as used herein alone or as part of another group refers to a —S(O)$_2$NR$_a$R$_b$ radical, where R$_a$ and R$_b$ are any suitable substituent such as H, alkyl, cycloalkyl, alkenyl, alkynyl or aryl.

"Urea" as used herein alone or as part of another group refers to an —N(R$_c$)C(O)NR$_a$R$_b$ radical, where R$_a$, R$_b$ and R$_c$ are any suitable substituent such as H, alkyl, cycloalkyl, alkenyl, alkynyl or aryl.

"Alkoxyacylamino" as used herein alone or as part of another group refers to an —N(R$_a$)C(O)OR$_b$ radical, where R$_a$, R$_b$ are any suitable substituent such as H, alkyl, cycloalkyl, alkenyl, alkynyl or aryl.

"Aminoacyloxy" as used herein alone or as part of another group refers to an —OC(O)NR$_a$R$_b$ radical, where R$_a$ and R$_b$ are any suitable substituent such as H, alkyl, cycloalkyl, alkenyl, alkynyl or aryl.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is generic and intended to include heterocyclic groups as discussed below unless specified otherwise.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O) $_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O) $_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3. Preferred heterocyclo groups include pyridyl and imidazolyl groups, these terms including the the quaternized derivatives thereof, including but not limited to quaternary pyridyl and imidazolyl groups, examples of which include but are not limited to:

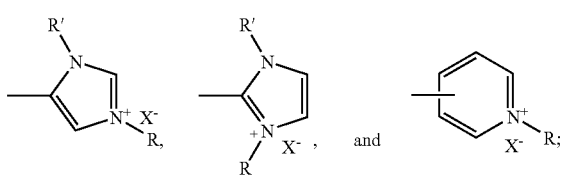

where R and R' are each a suitable substitutent as described in connection with "alkyl" above, and particularly alkyl (such as methyl, ethyl or propyl), arylalkyl (such as benzyl), optionally substituted with hydroxy (—OH), phosphonic acid (—PO$_3$H$_2$) or sulfonic acid (—SO$_3$H), and X$^-$ is a counterion.

"Spiroalkyl" as used herein alone or as part of another group, refers to a straight or branched chain hydrocarbon, saturated or unsaturated, containing from 3 to 8 carbon atoms. Representative examples include, but are not limited to, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CHCHCH$_2$—, —CH$_2$CH$_2$CH$_2$CH$_2$CH$_2$CH$_2$—, etc. The term "spiroalkyl" is intended to include both substituted and unsubstituted "spiroalkyl" unless otherwise indicated and these groups may be substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1 or 2.

"Treatment" as used herein means any manner in which one or more of the symptoms of a disease or disorder are ameliorated or otherwise beneficially altered. Treatment also encompasses any pharmaceutical use of the compositions herein, such as use for treating hyperproliferating tissue or neovascularization mediated diseases or disorders, or diseases or disorders in which hyperproliferating tissue or neovascularization is implicated. As used herein, amelioration of the symptoms of a particular disorder by administration of a particular compound or pharmaceutical composition refers to any lessening, whether permanent or temporary, lasting or transient that can be attributed to or associated with administration of the composition.

"Prodrug" as used herein is a compound that, upon in vivo administration, is metabolized by one or more steps or processes or otherwise converted to the biologically, pharmaceutically or therapeutically active form of the compound.

"Antibody" as used herein refers generally to immunoglobulins or fragments thereof that specifically bind to antigens to form immune complexes. The antibody may be whole immunoglobulin of any class, e.g., IgG, IgM, IgA, IgD, IgE, chimeric or hybrid antibodies with dual or multiple antigen or epitope specificities. It can be a polyclonal antibody, preferably an affinity-purified antibody from a human or an appropriate animal, e.g., a primate, goat, rabbit, mouse or the like. Monoclonal antibodies are also suitable for use in the present invention, and are preferred because of their high specificities. They are readily prepared by what are now considered conventional procedures of immunization of mammals with immunogenic antigen preparation, fusion of immune lymph or spleen cells with an immortal myeloma cell line, and isolation of specific hybridoma clones. More unconventional methods of preparing monoclonal antibodies are not excluded, such as interspecies fusions and genetic engineering manipulations of hypervariable regions, since it is primarily the antigen specificity of the antibodies that affects their utility. Newer techniques for production of monoclonals can also be used, e.g., human monoclonals, interspecies monoclonals, chimeric (e.g., human/mouse) monoclonals, genetically engineered antibodies and the like.

"Infecting agent" as used herein denotes invading microbes or parasites. As used herein, "microbe" denotes virus, bacteria, rickettsia, mycoplasma, protozoa, fungi and like microorganisms, and "parasite" denotes infectious, generally microscopic or very small multicellular invertebrates, or ova or juvenile forms thereof, which are susceptible to antibody-induced clearance or lytic or phagocytic destruction, e.g., malarial parasites, spirochetes and the like.

"Tumor" as used herein denotes a neoplasm, and includes both benign and malignant tumors. This term particularly includes malignant tumors which can be either solid (such as a breast, liver, or prostate carcinoma) or non-solid (such as a leukemia). Tumors can also be further divided into subtypes, such as adenocarcinomas (e.g. of the breast, prostate or lung).

"Target" as used herein denotes the object that is intended to be detected, diagnosed, impaired or destroyed by the methods provided herein, and includes target cells, target tissues, and target compositions. "Target tissues" and "target cells" as used herein are those tissues that are intended to be impaired or destroyed by this treatment method. Photosensitizing compounds bind to or collect in these target tissues or target cells; then when sufficient radiation is applied, these tissues or cells are impaired or destroyed. Target cells are cells in target tissue, and the target tissue includes, but is not limited to, vascular endothelial tissue, abnormal vascular walls of tumors, solid tumors such as (but not limited to) tumors of the head and neck, tumors of the eye, tumors of the gastrointestinal tract, tumors of the liver, tumors of the breast, tumors of the prostate, tumors of the lung, nonsolid tumors and malignant cells of the hematopoietic and lymphoid tissue, neovascular tissue, other lesions in the vascular system, bone marrow, and tissue or cells related to autoimmune disease. Also included among target cells are cells undergoing substantially more rapid division as compared to non-target cells.

"Non-target tissues" as used herein are all the tissues of the subject which are not intended to be impaired or destroyed by the treatment method. These non-target tissues include but are not limited to healthy blood cells, and other normal tissue, not otherwise identified to be targeted.

"Target compositions" as used herein are those compositions that are intended to be impaired or destroyed by this treatment method, and may include one or more pathogenic agents, including but not limited to bacteria, viruses, fungi, protozoa, and toxins as well as cells and tissues infected or infiltrated therewith. The term "target compositions" also includes, but is not limited to, infectious organic particles such as prions, toxins, peptides, polymers, and other compounds that may be selectively and specifically identified as an organic target that is intended to be impaired or destroyed by this treatment method.

"Hyperproliferative tissue" as used herein means tissue that grows out of control and includes neoplastic tissue, tumors and unbridled vessel growth such as blood vessel growth found in age-related macular degeneration and often occurring after glaucoma surgeries.

"Hyperproliferative disorders" as used herein denotes those conditions disorders sharing as an underlying pathology excessive cell proliferation caused by unregulated or abnormal cell growth, and include uncontrolled angiogenesis. Examples of such hyperproliferative disorders include, but are not limited to, cancers or carcinomas, acute and membrano-proliferative glomerulonephritis, myelomas, psoriasis, atherosclerosis, psoriatic arthritis, rheumatoid arthritis, diabetic retinopathies, macular degeneration, corneal neovascularization, choroidal hemangioma, recurrence of pterygii, and scarring from excimer laser surgery and glaucoma filtering surgery.

"Therapeutically effective dose" as used herein is a dose sufficient to prevent advancement, or to cause regression of the disease, or which is capable of relieving symptoms caused by the disease.

"Irradiating" and "irradiation" as used herein includes exposing a subject to all wavelengths of light. Preferably, the irradiating wavelength is selected to match the wavelength(s) which excite the photosensitive compound. Preferably, the radiation wavelength matches the excitation wavelength of the photosensitive compound and has low absorption by the non-target tissues of the subject, including blood proteins.

"Biological materials" as used herein refers to both tissues (such as biopsy tissues) and cells, as well as biological fluids such as blood, urine, plasma, cerebrospinal fluid, mucus, sputum, etc.

Irradiation is further defined herein by its coherence (laser) or non-coherence (non-laser), as well as intensity, duration, and timing with respect to dosing using the photosensitizing compound. The intensity or fluence rate must be sufficient for the light to reach the target tissue. The duration or total fluence dose must be sufficient to photoactivate enough photosensitizing compound to act on the target tissue. Timing with respect to dosing with the photosensitizing compound is important, because 1) the administered photosensitizing compound requires some time to home in on target tissue and 2) the blood level of many photosensitizing compounds decreases with time. The radiation energy is provided by an energy source, such as a laser or cold cathode light source, that is external to the subject, or that is implanted in the subject, or that is introduced into a subject, such as by a catheter, optical fiber or by ingesting the light source in capsule or pill form (e.g., as disclosed in. U.S. Pat. No. 6,273,904 (2001)).

While one preferred embodiment of the present invention is drawn to the use of light energy for administering photodynamic therapy (PDT) to destroy tumors, other forms of energy are within the scope of this invention, as will be understood by those of ordinary skill in the art. Such forms of energy include, but are not limited to: thermal, sonic, ultrasonic, chemical, light, microwave, ionizing (such as x-ray and gamma ray), mechanical, and electrical. For example, sonodynamically induced or activated agents include, but are not limited to: gallium-porphyrin complex (see Yumita et al., Cancer Letters 112: 79-86 (1997)), other porphyrin complexes, such as protoporphyrin and hematoporphyrin (see Umemura et al., Ultrasonics Sonochemistry 3: S187-S191 (1996)); other cancer drugs, such as daunorubicin and adriamycin, used in the presence of ultrasound therapy (see Yumita et al., Japan J. Hyperthermic Oncology 3(2):175-182 (1987)).

"Coupling agent" as used herein, refers to a reagent capable of coupling a photosensitizer to a targeting agent "Targeting agent" refers to a compound that homes in on or preferentially associates or binds to a particular tissue, receptor, infecting agent or other area of the body of the subject to be treated, such as a target tissue or target composition. Examples of a targeting agent include but are not limited to an antibody, a ligand, one member of a ligand-receptor binding pair, nucleic acids, proteins and peptides, and liposomal suspensions, including tissue-targeted liposomes.

"Specific binding pair" and "ligand-receptor binding pair" as used herein refers to two different molecules, where one of the molecules has an area on the surface or in a cavity which specifically attracts or binds to a particular spatial or polar organization of the other molecule, causing both molecules to have an affinity for each other. The members of the specific binding pair are referred to as ligand and receptor (antiligand). The terms ligand and receptor are intended to encompass the entire ligand or receptor or portions thereof sufficient for binding to occur between the ligand and the receptor. Examples of ligand-receptor binding pairs include, but are not limited to, hormones and hormone receptors, for example epidermal growth factor and epidermal growth factor receptor, tumor necrosis factor-.alpha. and tumor necrosis factor-receptor, and interferon and interferon receptor; avidin and biotin or antibiotin; antibody and antigen pairs; enzymes and substrates, drug and drug receptor; cell-surface antigen and lectin; two complementary nucleic acid strands; nucleic acid strands and complementary oligonucleotides; interleukin and interleukin receptor; and stimulating factors and their receptors, such as granulocyte-macrophage colony stimulating factor (GMCSF) and GMCSF receptor and macrophage colony stimulating factor (MCSF) and MCSF receptor.

"Linkers" are aromatic or aliphatic groups (which may be substituted or unsubstituted and may optionally contain heteroatoms such as N, O, or S) that are utilized to couple a bioconjugatable group, cross-coupling group, surface attachment group, hydrophilic group or the like to the parent molecule. Examples include but are not limited to aryl, alkyl, heteroaryl, heteroalkyl (e.g., oligoethylene glycol), peptide, and polysaccharide linkers, etc.

Subjects to be treated by the methods of the present invention for diagnostic or therapeutic purposes include both human subjects and animal subjects (particularly mammalian subjects such as dogs, cats, horses, monkeys, chimpanzees, etc.) for veterinary purposes.

The disclosures of all United States patent references cited herein are to be incorporated by reference herein as if fully set forth.

1. Compounds and Methods of Making.

As noted above, an aspect of the present invention is a method of making a compound of Formula I:

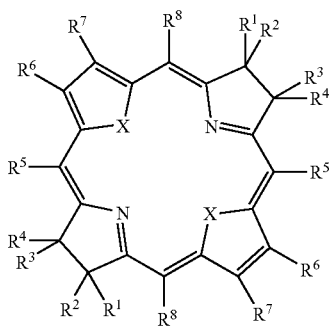

(I)

wherein:

X is selected from the group consisting of Se, NH, $CH_2$, O and S;

$R^1$, $R^2$, $R^3$, $R^4$, $R^5$, $R^6$, $R^7$ and $R^8$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, linking groups, and surface attachment groups;

or $R^1$ and $R^2$ together are =O or spiroalkyl (in which case preferably neither $R^3$ nor $R^4$ is H);

or $R^3$ and $R^4$ together are =O or spiroalkyl (in which case preferably neither $R^1$ nor $R^2$ is H);

optionally but preferably subject to the proviso that (i) neither $R^1$ nor $R^2$ is H, or (ii) neither $R^3$ nor $R^4$ is H; and $R^8$ is H or as given above;

the method comprising self-condensing a compound (or condensing a pair of compounds) of Formula II:

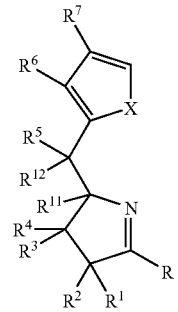

(II)

in an organic solvent in the presence of an acid to produce the compound of Formula I, wherein:

R is an acetal group;

X and $R^1$ to $R^7$ are as given above and $R^8$ is H; and $R^{11}$ and $R^{12}$ are each H; or $R^{11}$ and $R^{12}$ together form a covalent bond.

Optionally, $R^8$ is further substituted to replace H with additional substituents as described above in accordance with known techniques.

It will be appreciated that when a single compound is self-condensed, the various groups $R^1$ through $R^7$ will be symmetric in the compounds of Formula I, but that when a pair of compounds with different patterns of substituents are condensed, the various groups $R^1$ through $R^7$ may be unsymmetric or different in the compounds of Formula I).

In some embodiments, $R^1$, $R^2$, $R^3$, and $R^4$ are preferably each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, alkoxy, carboxylic acid, hydroxyl, alkylthio, amino, alkylamino, arylalkylamino, disubstituted amino, acylamino, acyloxy, ester, In some embodiments, $R^1$, $R^2$, $R^3$, and $R^4$ are most preferably each independently selected from the group consisting of H and alkyl.

In some embodiments, preferably, $R^1$ and $R^2$ are each independently selected from the group consisting of H, alkyl, cycloalkyl, aryl, alkoxy, halo, mercapto, hydroxyl, nitro, acyl, alkoxy, alkylthio, amino, alkylamino, arylalkylamino, disubstituted amino, acylamino, acyloxy, amide, sulfonamide, urea, alkoxylacylamino, aminoacyloxy, and linking groups. Most preferably $R^1$ and $R^2$ are each independently selected from the group consisting of H, alkyl, aryl, alkoxy, halo, mercapto, cyano, hydroxyl, nitro, acyl, alkoxy, alkylthio, alkylamino, acyloxy, amide, and linking groups. In some embodiments $R^1$ and $R^2$ are preferably not H, alkyl or cycloalkyl ("cycloalkyl" including heterocyclo), particularly not alkyl or cycloalkyl, and most particularly one is not alkyl when the other is cycloalkyl.

In some embodiments, preferably, $R^3$ and $R^4$ are each independently selected from the group consisting of alkyl, alkenyl, alkynyl, cycloalkyl, cycloalkylalkyl, cycloalkylalkenyl, cycloalkylalkynyl, aryl, arylalkyl, arylalkenyl, arylalkynyl, and linking groups. Most preferably, $R^3$ and $R^4$ are each independently selected from the group consisting of alkyl, cycloalkyl, aryl, arylalkyl, and linking groups.

In some embodiments, preferably, $R^5$ is selected from the group consisting of H, alkyl, alkenyl, alkynyl, cycloalkyl, cycloalkylalkyl, cycloalkylalkenyl, cycloalkylalkynyl, aryl, arylalkyl, arylalkenyl, arylalkynyl, alkoxy, halo, cyano, nitro, acyl, alkoxy, alkylthio, amino, alkylamino, arylalkylamino, disubstituted amino, acylamino, acyloxy, amide, sulfonamide, urea, alkoxyacylamino, aminoacyloxy, and linking groups. Most preferably, $R^5$ is selected from the group consisting of H, alkyl, alkenyl, alkynyl, cycloalkyl, aryl, arylalkyl, arylalkenyl, arylalkynyl, alkoxy, halo, cyano, nitro, acyl, alkoxy, alkylthio, alkylamino, arylalkylamino, disubstituted amino, acylamino, acyloxy, amide, and linking groups.

In some embodiments $R^5$ is preferably not H or alkyl, and particularly not H.

In some embodiments, preferably, $R^6$ and $R^7$ are each independently selected from the group consisting of H, alkyl, alkenyl, alkynyl, cycloalkyl, cycloalkylalkyl, cycloalkylalkenyl, cycloalkylalkynyl, aryl, arylalkyl, arylalkenyl, arylalkynyl, alkoxy, halo, cyano, nitro, acyl, alkoxy, alkylthio, amino, alkylamino, arylalkylamino, disubstituted amino, acylamino, acyloxy, amide, sulfonamide, urea, alkoxyacylamino, aminoacyloxy, and linking groups. Most preferably, $R^6$ and $R^7$ are each independently selected from the group consisting of H, alkyl, alkenyl, alkynyl, cycloalkyl, aryl, arylalkyl, arylalkenyl, arylalkynyl, alkoxy, halo, cyano, nitro, acyl, alkoxy, alkylthio, alkylamino, arylalkylamino, disubstituted amino, acylamino, acyloxy, amide, and linking groups.

In some embodiments at least one or both $R^6$ is preferably neither H nor alkyl, and particularly not H.

In some embodiments at least one or both $R^7$ is preferably neither H nor alkyl, and particularly not methyl.

In some embodiments, preferably, $R^8$ is selected from the group consisting of H, alkyl, alkenyl, alkynyl, cycloalkyl, cycloalkylalkyl, cycloalkylalkenyl, cycloalkylalkynyl, aryl, arylalkyl, arylalkenyl, arylalkynyl, alkoxy, halo, cyano, nitro, acyl, alkoxy, alkylthio, amino, alkylamino, arylalkylamino, disubstituted amino, acylamino, acyloxy, amide, sulfonamide, urea, alkoxyacylamino, aminoacyloxy, and linking groups. Most preferably, $R^8$ is selected from the group consisting of H, alkyl, alkenyl, alkynyl, cycloalkyl, aryl, arylalkyl, arylalkenyl, arylalkynyl, alkoxy, halo, cyano, nitro, acyl, alkoxy, alkylthio, alkylamino, arylalkylamino, disubstituted amino, acylamino, acyloxy, amide, and linking groups.

In some embodiments $R^8$ is preferably not H or alkyl, and particularly not H.

In some embodiments compounds of Formula I are subject to the proviso that, when X is NH: $R^1$ is not cycloalkyl; or $R^2$ is not methyl; or R is not H; or $R^6$ is not H; or $R^7$ is not methyl.

Synthesis via acetal intermediates. Compounds of Formula I are made from compounds of Formula IIa or IIb as shown below by treating the compounds of Formulas IIa or IIb with an acid in an organic solvent. The acid is not critical, with examples including but not limited to $BF_3$ etherate, $SnCl_4$, $InCl_3$, trifluoroacetic acid, and toluenesulfonic acid. The organic solvent is not critical with examples including but not limited to acetonitrile, methylene chloride, chloroform, tetrahydrofuran, chlorobenzene, ethanol, and combinations thereof. The reaction may be carried out at any suitable temperature, such as 0 to 100° C., and conveniently at room temperature, for any suitable time period, such as for a few minutes, 1 to 4 hours, or a day. The reaction mixture is preferably nonaqueous but need not be anhydrous, and may conveniently be carried out exposed to air. When compounds of Formula IIb are utilized the reaction mixture preferably includes an oxidizing agent such as air or DDQ.

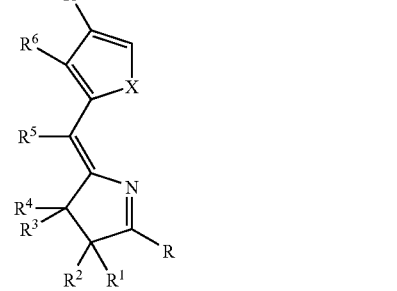

(IIa)

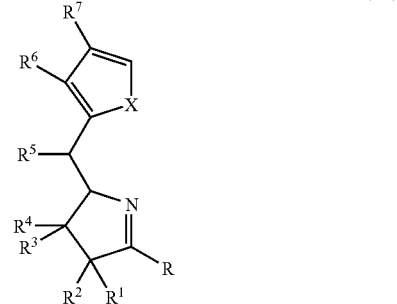

(IIb)

in Formulas IIa and IIb, $R^1$ through $R^7$ are the same as given above in connection with Formula I, and R is acetal.

Compounds of Formulas IIa and IIb are made from compounds of Formula III.

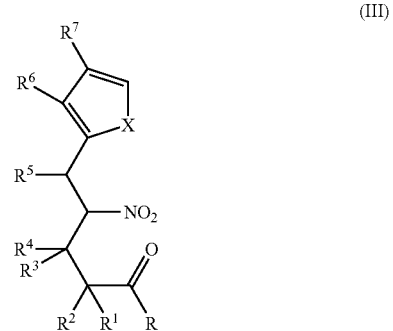

(III)

$R^1$ through $R^7$ are the same as given above in connection with Formula I, and R is acetal. In general, compounds of Formula IIa are produced by deprotonating a compound of Formula III (e.g., by treating with anhydrous sodium methoxide) to produce a nitronate anion intermediate, and then cyclizing the intermediate with a deoxygenating agent (e.g., by combining the intermediate with an aqueous buffered $TiCl_3$ solution) to produce the compound of Formula IIa. Reaction conditions are not critical and numerous variations will be apparent to those skilled in the art. In general, compounds of Formula IIb are produced by treating a compound of Formula III with a metal (e.g., zinc and acetic acid in ethanol) to produce an N-oxide intermediate, and then cyclizing the intermediate with a deoxygenating agent (eg., Ti(0), Zn, NaOH/methanol; Zn, aqueous $NH_4Cl$/THF; $FeSO_4$, aqueous $NH_4Cl/CH_3CN$; Mg or Fe, $AcONH_4$/methanol; $Ph_3P$/toluene; S/toluene; $NaN_3$/toluene; Zn, NaI, $Me_3SiCl/CH_3CN$; etc.) to produce the compound of Formula IIb. Again reaction conditions are not critical and numerous variations will be apparent to those skilled in the art.

Synthesis via aldehyde intermediates. Compounds of Formula I are made from compounds of Formula IIa or IIb as shown above, where R is an aldehyde, by treating the compounds of Formulas IIa or IIb with an acid in an organic solvent in like manner as described above. Compounds of Formula IIa or IIb where R is an aldehyde are made by oxidizing a corresponding compound of Formula V:

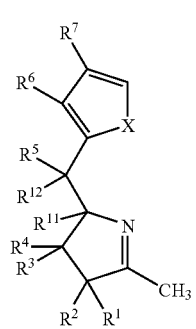

in an organic solvent in the presence of an oxidizing agent to produce the compound of Formula II. Any suitable solvent can be used, particularly ethereal solvents such as 1,4-dioxane, tetrahydrofuran, diethyl ether and dimethoxyethane. The reaction conditions are not critical and the reaction may be carried out at any suitable temperature, for example 0 to 100° C., preferably room temperature, for any suitable time, typically one to two hours. $SeO_2$ is currently preferred as the oxidizing agent, but any suitable oxidizing agent may be used. In general, when relatively powerful oxidizing agents are employed with alkyl groups that are activated by the presence of a π bond (allylic), the alkyl group can be oxidized to the aldehyde or ketone. The most common reagents for these transformations are selenium dioxide ($SeO_2$), chromium trioxide ($CrO_3$), chromyl chloride ($CrO_2Cl_2$), and $Pb(OAc)_4$. In addition, t-BuOOH/CuI oxidizes the allylic carbon of alkenyl conjugated ketones (Organic Synthesis, $2^{nd}$ Ed; Smith, M. B.; McGraw-Hill Higher Education: 2002; 272-279) and can also be used as oxidizing agents herein. A variety of chromium reagents have been used for allylic oxidations ((a) Dauben, W. G.; Lorber, M.; Fullerton, D. S. *J. Org. Chem.* 1969, 34, 3587-3592. (b) Fullerton, D. S.; Chen, C. M. *Synth. Commun.* 1976, 6, 217-220. (c) Salmond, W. G.; Barta, M. A.; Havens, J. L. *J. Org. Chem.* 1978, 43, 2057-2059. (d) Parish, E. J.; Chitrakorn, S.; Wei, T.-Y. *Synth. Commun.* 1986, 16, 1371-1375. (e) Parish, E. J.; Wei, T.-Y. *Synth. Commun.* 1987, 17, 1227-1233. (f) Marshall, C. W.; Ray, R. E.; Laos, I.; Riegel, B. *J. Am. Chem. Soc.* 1975, 79, 6308-6313. (g) Amann, A.; Ourisson, G.; Luu, B. *Synthesis* 1987, 1002-1005. (h) Bora, U.; Chaudhuri, M. K.; Dey, D.; Kalita, D.; Kharmawphlang, W.; Mandal, G. C. *Tetrahedron* 2001, 57, 2445-2448) and can also be used as oxidizing agents herein. Examples include $CrO_3$-pyridine complex, $CrO_3$ and 3,5-dimethylpyrazole, pyridinium chlorochromate (PCC), pyridinium dichromate (PDC), sodium chromate, sodium dichromate in acetic acid, pyridinium fluorochromate, and 3,5-dimethylpyrazolium fluorochromate (VI). The 5-methyl group of a pyrrole-2-ester was oxidized by ceric ammonium nitrate ((a) Huggins, M. T.; Lightner, D. A. *Tetrahedron* 2000, 56, 1797-1810. (b) Tipton, A. K.; Lightner, D. A.; McDonagh, A. F. *J. Org. Chem.* 2001, 66, 1832-1838) and this can also be used as an oxidizing agent herein.

Compounds of Formula I may be produced wherein $R^8$ is H by the methods described above, and then $R^8$ brominated in accordance with known techniques and further substituents added at position $R^8$ in accordance with known techniques. Likewise other substituents can be added at positions $R^1$ through $R^7$ by substitution (e.g., by bromination or formylation) in accordance with known techniques.

Compounds of Formula I may be metalated with any suitable metal in accordance with known techniques. See, e.g., U.S. Pat. No. 6,208,553. Suitable metals include but are not limited to Pd(II), Pt(II), Mg(II), Zn(II), Al(III), Ga(III), In(III), Sn(IV), Cu(II), Ni(II), and Au(III). Where the metal is trivalent or tetravalent a counterion is included as necessary in accordance with known techniques.

Linking groups for conjugates. Linking groups are included in compounds of Formula I to provide a reactive site for conjugation so that the compounds may be coupled to or conjugated to other groups such as proteins, peptides, targeting agents such as antibodies, polymers, particles such as nanoparticles, organic, polymeric or inorganic beads, other solid support surfaces, etc., to form additional active compounds of the invention. In general each group is attached to a linking group including a linker which can be aryl, alkyl, heteroaryl, heteroalkyl (e.g., oligoethylene glycol), peptide, polysaccharide, etc. The linking group may be simply a reactive attachment group or moiety (e.g., —R' where R' is a reactive group such as bromo), or may comprise a combination of an intervening group coupled to a reactive group (e.g., —R"R', where R' is a reactive group and R' is an intervening group such as a hydrophilic group).

For bioconjugation purposes, the choice of water-solubilizing group(s) and conjugation groups is made so as to achieve orthogonal coupling. For example, if a carboxylic acid is used for water solubility, an aldehyde might be used for bioconjugation (via reductive amination with an amino-substituted biomolecule). If a carboxylic acid is used for bioconjugation (via carbodiimide-activation and coupling with an amino-substituted biomolecule), then a complementary group can be used for water solubility (e.g., sulfonic acid, guanidinium, pyridinium). Bioconjugatable groups include amines (including amine derivatives) such as isocyanates, isothiocyanates, iodoacetamides, azides, diazonium salts, etc. acids or acid derivatives such as N-hydroxysuccinimide esters (more generally, active esters derived from carboxylic acids; e.g., p-nitrophenyl ester), acid hydrazides, etc., and other linking groups such as aldehydes, sulfonyl chlorides, sulfonyl hydrazides, epoxides, hydroxyl groups, thiol groups, maleimides, aziridines, acryloyls, halo groups, biotin, 2-Iminobiotin, etc. Linking groups such as the foregoing are known and described in U.S. Pat. Nos. 6,728,129; 6,657,884; 6,212, 093; and 6,208,553.

Conjugates. Other groups can be attached to the bacteriochlorin to form a conjugate by means of a linking group to tune or adjust the solubility properties of the bacteriochlorin, including hydrophobic groups, hydrophilic groups, polar groups, or amphipathic groups. The polar groups include carboxylic acid, sulfonic acid, guanidinium, carbohydrate, hydroxy, amino acid, pyridinium, imidazolium, etc. Such groups can be attached to substituents that are linear or branched alkyl (e.g., swallowtail), aryl, heteroaryl, heteroalkyl (e.g., oligoethylene glycol), peptide, polysaccharide, etc. Targeting groups such as antibodies, proteins, peptides, and nucleic acids may be attached by means of the linking group. Particles such as nanoparticles, glass beads, etc. may be attached by means of the linking group. Where such additional compounds are attached to form a conjugate that may be attached directly to the bacteriochlorin or attached by means of an intervening group such as a hydrophilic group, depending upon the particular linking group employed (as noted above).

Hydrophilic groups. Compounds of the present invention may include hydrophilic groups coupled at the linking sites noted above, e.g., covalently coupled thereto, to facilitate delivery thereof, or improve stability, in accordance with known techniques (e.g., to the N-terminus of the peptide). Suitable hydrophilic groups are typically polyols or polyalkylene oxide groups, including straight and branched-chain polyols, with particularly examples including but not limited to poly(propylene glycol), polyethylene-polypropylene glycol or poly(ethylene glycol). The hydrophilic groups may have a number average molecular weight of 20,000 to 40,000 or 60,000. Suitable hydrophilic groups and the manner of coupling thereof are known and described in, for example, U.S. Pat. Nos. 4,179,337; 5,681,811; 6,524,570; 6,656,906; 6,716,811; and 6,720,306. For example, compounds can be pegylated using a single 40,000 molecular weight polyethylene glycol moiety that is attached to the compound by means of a linking group.

Surface attachment groups. As noted above, compounds of the invention can be substituted with a surface attachment group, which may be in protected or unprotected form. A surface attachment group may be a reactive group coupled directly to the bacteriochlorin, or coupled to the bacteriochlorin by means of an intervening linker. Linkers L can be aryl, alkyl, heteroaryl, heteroalkyl (e.g., oligoethylene glycol), peptide, polysaccharide, etc. Examples of surface attachment groups (with the reactive site or group in unprotected form) include but are not limited to alkene, alkyne, alcohol, thiol, selenyl, phosphono, telluryl, cyano, amino, formyl, halo, boryl, and carboxylic acid surface attachment groups such as:

4-carboxyphenyl, carboxymethyl, 2-carboxyethyl, 3-carboxypropyl, 2-(4-carboxyphenyl)ethynyl, 4-(2-(4-carboxyphenyl)ethynyl)phenyl, 4-carboxymethylphenyl, 4-(3-carboxypropyl)phenyl, 4-(2-(4-carboxymethylphenyl)ethynyl)phenyl; 4-hydroxyphenyl, hydroxymethyl, 2-hydroxyethyl, 3-hydroxypropyl, 2-(4-hydroxyphenyl)ethynyl, 4-(2-(4-hydroxyphenyl)ethynyl)phenyl, 4-hydroxymethylphenyl, 4-(2-hydroxyethyl)phenyl, 4-(3-hydroxypropyl)phenyl, 4-(2-(4-hydroxymethylphenyl)ethynyl)phenyl; 4-mercaptophenyl, mercaptomethyl, 2-mercaptoethyl, 3-mercaptopropyl, 2-(4-mercaptophenyl)ethynyl, 4-(2-(4-mercaptophenyl)ethynyl)phenyl, 4-mercaptomethylphenyl, 4-(2-mercaptoethyl)phenyl, 4-(3-mercaptopropyl)phenyl, 4-(2-(4-mercaptomethylphenyl)ethynyl)phenyl; 4-selenylphenyl, selenylmethyl, 2-selenylethyl, 3-selenylpropyl, 2-(4-selenylphenyl)ethynyl, 4-selenylmethylphenyl, 4-(2-selenylethyl)phenyl, 4-(3-selenylpropyl)phenyl, 4-selenylmethylphenyl, 4-(2-(4-selenylphenyl)ethynyl)phenyl; 4-tellurylphenyl, tellurylmethyl, 2-tellurylethyl, 3-tellurylpropyl, 2-(4-tellurylphenyl)ethynyl, 4-(2-(4-tellurylphenyl)ethynyl)phenyl, 4-tellurylmethylphenyl, 4-(2-tellurylethyl)phenyl, 4-(3-tellurylpropyl)phenyl, 4-(2-(4-tellurylmethylphenyl)ethynyl)phenyl;

4-(dihydroxyphosphoryl)phenyl, (dihydroxyphosphoryl)methyl, 2-(dihydroxyphosphoryl)ethyl, 3-(dihydroxyphosphoryl)propyl, 2-[4-(dihydroxyphosphoryl)phenyl]ethynyl, 4-[2-[4-(dihydroxyphosphoryl)phenyl]ethynyl]phenyl, 4-[(dihydroxyphosphoryl)methyl]phenyl, 4-[2-(dihydroxyphosphoryl)ethyl]phenyl, 4-[2-[4-(dihydroxyphosphoryl)methylphenyl]ethynyl]phenyl; 4-(hydroxy(mercapto)phosphoryl)phenyl, (hydroxy(mercapto)phosphoryl)methyl, 2-(hydroxy(mercapto)phosphoryl)ethyl, 3-(hydroxy(mercapto)phosphoryl)propyl, 2-[4-(hydroxy(mercapto)phosphoryl)phenyl]ethynyl, 4-[2-[4-(hydroxy(mercapto)phosphoryl)phenyl]ethynyl]phenyl, 4-[(hydroxy(mercapto)phosphoryl)methyl]phenyl, 4-[2-(hydroxy(mercapto)phosphoryl)ethyl]phenyl, 4-[2-[4-(hydroxy(mercapto)phosphoryl)methylphenyl]ethynyl]phenyl;

4-cyanophenyl, cyanomethyl, 2-cyanoethyl, 3-cyanopropyl, 2-(4-cyanophenyl)ethynyl, 4-[2-(4-cyanophenyl)ethynyl]phenyl, 4-(cyanomethyl)phenyl, 4-(2-cyanoethyl)phenyl, 4-[2-[4-(cyanomethyl)phenyl]ethynyl]phenyl;

4-cyanobiphenyl; 4-aminophenyl, aminomethyl, 2-aminoethyl, 3-aminopropyl, 2-(4-aminophenyl)ethynyl, 4-[2-(4-aminophenyl)ethynyl]phenyl, 4-aminobiphenyl;

4-formylphenyl, 4-bromophenyl, 4-iodophenyl, 4-vinylphenyl, 4-ethynylphenyl, 4-allylphenyl, 4-[2-(trimethylsilyl)ethynyl]phenyl, 4-[2-(triisopropylsilyl)ethynyl]phenyl, 4-(4,4,5,5-tetramethyl-1,3,2-dioxaborolan-2-yl)phenyl;

formyl, bromo, iodo, bromomethyl, chloromethyl, ethynyl, vinyl, allyl; 4-(ethynyl)biphen-4'-yl, 4-[2-(triisopropylsilyl)ethynyl]biphen-4'-yl, 3,5-diethynylphenyl;

4-(bromomethyl)phenyl, and 2-bromoethyl.

In addition to the monodentate linker-surface attachment groups described above, multidentate linkers can be employed [Nikitin, K. *Chem. Commun.* 2003, 282-283; Hu, J.; Mattem, D. L. *J. Org. Chem.* 2000, 65, 2277-2281; Yao, Y.; Tour, J. M. *J. Org. Chem.* 1999, 64, 1968-1971; Fox, M. A. et al. *Langmuir,* 1998, 14, 816-820; Galoppini, E.; Guo, W. *J. Am. Chem. Soc.* 2001, 123, 4342-4343; Deng, X. et al. *J. Org. Chem.* 2002, 67, 5279-5283; Hector Jr., L. G. et al. *Surface Science,* 2001, 494, 1-20; Whitesell, J. K.; Chang, H. K. *Science,* 1993, 261, 73-76; Galoppini, E. et al. *J. Am. Chem. Soc.* 2002, 67, 7801-7811; Siiman, O. et al. *Bioconjugate Chem.* 2000, 11, 549-556]. Tripodal linkers bearing thiol, carboxylic acid, alcohol, or phosphonic acid units are particularly attractive for firmly anchoring a molecular device on a planar surface. Specific examples of such linkers are built around the triphenylmethane or tetraphenylmethane unit, including the following:

1,1,1-tris[4-(S-acetylthiomethyl)phenyl]methyl,

4-{1,1,1-tris[4-(S-acetylthiomethyl)phenyl]methyl}phenyl, 1,1,1-tris[4-(dihydroxyphosphoryl)phenyl]methyl, 4-{1,1,1-tris[4-(dihydroxyphosphoryl)phenyl]methyl}phenyl, 1,1,1-tris[4-dihydroxyphosphorylmethyl)phenyl]methyl, and 4-{1,1,1-tris[4-(dihydroxyphosphorylmethyl)phenyl]methyl}phenyl;

All as described in Balakumar, Muthukumaran and Lindsey, U.S. patent application Ser. No. 10/867,512 (filed Jun. 14, 2004). See also Lindsey, Loewe, Muthukumaran, and Ambroise, US Patent Application Publication No. 20050096465 (Published May 5, 2005), particularly paragraph 51 thereof. Additional examples of multidentate linkers include but are not limited to:

Alkene surface attachment groups (2, 3, 4 carbons) such as:
3-vinylpenta-1,4-dien-3-yl,
4-(3-vinylpenta-1,4-dien-3-yl)phenyl,
4-(3-vinylpenta-1,4-dien-3-yl)biphen-4'-yl,
4-allylhepta-1,6-dien-4-yl,
4-(4-allylhepta-1,6-dien-4-yl)phenyl,
4-(4-allylhepta-1,6-dien-4-yl)biphen-4'-yl,
5-(1-buten-4-yl)nona-1,8-dien-5-yl,
4-[5-(1-buten-4-yl)nona-1,8-dien-5-yl]phenyl,
4-[5-(1-buten-4-yl)nona-1,8-dien-5-yl]biphen-4'-yl, etc.

Alkyne surface attachment groups (2, 3, 4 carbons) such as:
3-ethynylpenta-1,4-diyn-3-yl,
4-(3-ethynylpenta-1,4-diyn-3-yl)phenyl,
4-(3-ethynylpenta-1,4-diyn-3-yl)biphen-4'-yl,
4-propargylhepta-1,6-diyn-4-yl,
4-(4-propargylhepta-1,6-diyn-4-yl)phenyl,
4-(4-propargylhepta-1,6-diyn-4-yl)biphen-4'-yl,
5-(1-butyn-4-yl)nona-1,8-diyn-5-yl,
4-[5-(1-butyn-4-yl)nona-1,8-diyn-5-yl]phenyl,
4-[5-(1-butyn-4-yl)nona-1,8-diyn-5-yl]biphen-4'-yl, Alcohol surface attachment groups (1, 2, 3 carbons), such as:
2-(hydroxymethyl)-1,3-dihydroxyprop-2-yl,
4-[2-(hydroxymethyl)-1,3-dihydroxyprop-2-yl]phenyl,
4-[2-(hydroxymethyl)-1,3-dihydroxyprop-2-yl]biphen-4'-yl,
3-(2-hydroxyethyl)-1,5-dihydroxypent-3-yl,
4-[3-(2-hydroxyethyl)-1,5-dihydroxypent-3-yl]phenyl,
4-[3-(2-hydroxyethyl)-1,5-dihydroxypent-3-yl]biphen-4'-yl,
4-(3-hydroxypropyl)-1,7-dihydroxyhept-4-yl,
4-[4-(3-hydroxypropyl)-1,7-dihydroxyhept-4-yl]phenyl,
4-[4-(3-hydroxypropyl)-1,7-dihydroxyhept-4-yl]biphen-4'-yl, etc., Thiol surface attachment groups (1, 2, 3 carbons) such as:
2-(mercaptomethyl)-1,3-dimercaptoprop-2-yl,
4-[2-(mercaptomethyl)-1,3-dimercaptoprop-2-yl]phenyl,
4-[2-(mercaptomethyl)-1,3-dimercaptoprop-2-yl]biphen-4'-yl,
3-(2-mercaptoethyl)-1,5-dimercaptopent-3-yl
4-[3-(2-mercaptoethyl)-1,5-dimercaptopent-3-yl]phenyl,
4-[3-(2-mercaptoethyl)-1,5-dimercaptopent-3-yl]biphen-4'-yl,
4-(3-mercaptopropyl)-1,7-dimercaptohept-4-yl,
4-[4-(3-mercaptopropyl)-1,7-dimercaptohept-4-yl]phenyl,
4-[4-(3-mercaptopropyl)-1,7-dimercaptohept-4-yl]biphen-4'-yl etc., Selenyl surface attachment groups (1, 2, 3 carbons), such as:
2-(selenylmethyl)-1,3-diselenylprop-2-yl,
4-[2-(selenylmethyl)-1,3-diselenylprop-2-yl]phenyl,
4-[2-(mercaptomethyl)-1,3-dimercaptoprop-2-yl]biphen-4'-yl,
3-(2-selenylethyl)-1,5-diselenylpent-3-yl,
4-[3-(2-selenylethyl)-1,5-diselenylpent-3-yl]phenyl,
4-[3-(2-selenylethyl)-1,5-diselenylpent-3-yl]biphen-4'-yl,
4-(3-selenylpropyl)-1,7-diselenylhept-4-yl,
4-[4-(3-selenylpropyl)-1,7-diselenylhept-4-yl]phenyl,
4-[4-(3-selenylpropyl)-1,7-diselenylhept-4-yl]biphen-4'-yl, etc.

Phosphono surface attachment groups (1, 2, 3 carbons), such as:
2-(phosphonomethyl)-1,3-diphosphonoprop-2-yl,
4-[2-(phosphonomethyl)-1,3-diphosphonoprop-2-yl]phenyl,
4-[2-(phosphonomethyl)-1,3-diphosphonoprop-2-yl]biphen-4'-yl,
3-(2-phosphonoethyl)-1,5-diphosphonopent-3-yl,
4-[3-(2-phosphonoethyl)-1,5-diphosphonopent-3-yl]phenyl,
4-[3-(2-phosphonoethyl)-1,5-diphosphonopent-3-yl]biphen-4'-yl,
4-(3-phosphonopropyl)-1,7-diphosphonohept-4-yl,
4-[4-(3-phosphonopropyl)-1,7-diphosphonohept-4-yl]phenyl,
4-[4-(3-phosphonopropyl)-1,7-diphosphonohept-4-yl]biphen-4'-yl, etc., and Carboxylic acid surface attachment groups (1, 2, 3 carbons), such as:
2-(carboxymethyl)-1,3-dicarboxyprop-2-yl,
4-[2-(carboxymethyl)-1,3-dicarboxyprop-2-yl]phenyl,
4-[2-(carboxymethyl)-1,3-dicarboxyprop-2-yl]biphen-4'-yl,
3-(2-carboxyethyl)-1,5-dicarboxypent-3-yl,
4-[3-(2-carboxyethyl)-1,5-dicarboxypent-3-yl]phenyl,
4-[3-(2-carboxyethyl)-1,5-dicarboxypent-3-yl]biphen-4'-yl,
4-(3-carboxypropyl)-1,7-dicarboxyhept-4-yl,
4-[4-(3-carboxypropyl)-1,7-dicarboxyhept-4-yl]phenyl,
4-[4-(3-carboxypropyl)-1,7-dicarboxyhept-4-yl]biphen-4'-yl, etc.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

Active compounds of the invention can be provided as pharmaceutically acceptable salts. Such salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

Active compounds of the invention include prodrugs of the compounds described herein. As noted above, a "prodrug" is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

Utility. The methods and intermediates described herein are useful for the synthesis of compounds of Formula I as described herein. Such compounds are useful per se or in further modified form (e.g., as a salt, metalated compound, conjugate or prodrug) for diagnostic and therapeutic purposes in like manner as other compounds described for photodynamic therapy, such as described in US Patent Application Publication No. 2004/0044197 to Pandey et al. and as set forth in further detail below.

Stability. An advantage of the compounds of the present invention is their stability and absorption characteristics. Thus, the present invention provides a "neat" composition consisting of an active compound of the invention (e.g., compounds of Formula I, or the pharmaceutically acceptable salts, prodrugs, or conjugates thereof (e.g, with a targeting agent such as a protein, peptide or antibody)), wherein the composition has or is characterized by a peak Molar absorption coefficient in solution of at least 10,000, up to 300,000 $M^{-1}$ $cm^{-1}$ or more, at a wavelength between 650 and 850 or 900 nanometers (it being understood that (a) the active compound must be placed into solution to determine its peak Molar absorption coefficient at the indicated wavelength; and (b) the compound may exhibit additional peaks outside of this range, or multiple peaks within this range).

In addition, the present invention provides compositions comprising or consisting essentially of an active compound of the invention (e.g., compounds of Formula I, or the pharmaceutically acceptable salts, prodrugs, or conjugates thereof (e.g, with a targeting agent such as a protein, peptide or antibody)) in a solvent. The amount of solvent is not critical and may comprise from 0.01 or 1 to 99 or 99.99 percent by weight of the composition. The composition has or is characterized by a peak Molar absorption coefficient in solution of at least 10,000, up to 300,000 $M^{-1}$ $cm^{-1}$ or more, at a wavelength between 650 and 850 or 900 nanometers. It will be appreciated that agitation may be required to break agglomerated particles back into solution prior to determining molar absorption, but that some level of agglomeration may actually be desired for practical use of the composition. Suitable solvents depend upon the particular compound and intended use for that compound, but include both organic solvents, aqueous solvents and combinations thereof.

The compositions, be they the bacteriochlorin compounds in "neat" form or the compounds mixed with a solvent, have or exhibit a loss of not more than 10, 15 or 20 percent by weight of the bacteriochlorin compound of the invention (due to degredation thereof) when stored in a sealed vessel (e.g., a flask ampoule or vial), at room temperature in the absence of ambient light for at least 3 or 4 months. Degredation can be determined by spectroscopy, thin-layer chromatography, NMR spectroscopy, and/or mass spectrometry, in accordance with known techniques.

2. Pharmaceutical Formulations.

Formulation of Pharmaceutical Compositions. The pharmaceutical compositions provided herein contain therapeutically effective amounts of one or more of the compounds provided herein that are useful in the prevention, treatment, or amelioration of one or more of the symptoms of diseases or disorders associated with hyperproliferating tissue or neovascularization, or in which hyperproliferating tissue or neovascularization is implicated, in a pharmaceutically acceptable carrier. Diseases or disorders associated with hyperproliferating tissue or neovascularization include, but are not limited to, cancer, psoriasis, atherosclerosis, heart disease, and age-related macular degeneration. Pharmaceutical carriers suitable for administration of the compounds provided herein include any such carriers known to those skilled in the art to be suitable for the particular mode of administration.

Pharmaceutical compositions preferably exhibit the absorption characteristics and storage or stability characteristics described above.

In addition, the compounds may be formulated as the sole pharmaceutically active ingredient in the composition or may be combined with other active ingredients.

The compositions contain one or more compounds provided herein. The compounds are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel, Introduction to Pharmaceutical Dosage Forms, Fourth Edition 1985, 126).

In the compositions, effective concentrations of one or more compounds or pharmaceutically acceptable derivatives thereof is (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders associated with hyperproliferating tissue or neovascularization or in which hyperproliferating tissue or neovascularization is implicated.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and in U.S. Pat. No. 5,952,366 to Pandey et al. (1999) and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with hyperproliferating tissue or neovascularization or in which hyperproliferating tissue or neovascularization is implicated, as described herein.

In one embodiment, a therapeutically effective dosage should produce a serum concentration of active ingredient of from about 0.1 ng/ml to about 50-100 ug/ml. In one embodiment, a therapeutically effective dosage is from 0.001, 0.01 or 0.1 to 10, 100 or 1000 mg of active compound per kilogram of body weight per day. Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN™, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

Compositions for Oral Administration. Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

Solid Compositions for Oral Administration. In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polyinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, gellan gum, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient. When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid Compositions for Oral Administration. Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms. Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, xanthan gum, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation. For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. No. RE28,819 and U.S. Pat. No. 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

3. Injectables, Solutions and Emulsions. Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, xanthan gum, hydroxypropyl methylcellulose and polyvinylpyrrolidone. Emulsifying agents include Polysorbate 80 (TWEEN™ 80 emulsifying agent). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Lyophilized Powders. Lyophilized powders, which can be reconstituted for administration as solutions, emulsions and other mixtures, can also be used to carry out the present invention. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical Administration. Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044, 126; 4,414,209; and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracistemal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered. These solutions, particularly those intended for ophthalmic use, may be formulated as 0.01%-10% isotonic solutions, pH about 5-7, with appropriate salts.

Compositions for other Routes of Administration. Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983; 6,261,595; 6,256,533; 6,167,301; 6,024,975; 6,010,715; 5,985,317; 5,983,134; 5,948,433 and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

Targeted Formulations. The compounds provided herein, or pharmaceutically acceptable derivatives thereof, may also be formulated to be targeted to a particular tissue, receptor, infecting agent or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316, 652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542 and 5,709,874.

Liposomes. In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Ligands. In another embodiment, the disclosed compounds may be targeted to specific target tissues or target compositions using ligands specific for the target tissue or target composition, for example, using ligands or ligand-receptor pairs such as antibodies and antigens. Antibodies against tumor antigens and against pathogens are known. For example, antibodies and antibody fragments which specifically bind markers produced by or associated with tumors or infectious lesions, including viral, bacterial, fungal and parasitic infections, and antigens and products associated with such microorganisms have been disclosed, inter alia, in Hansen et al., U.S. Pat. No. 3,927,193 and Goldenberg, U.S. Pat. Nos. 4,331,647; 4,348,376; 4,361,544; 4,468,457; 4,444, 744; 4,818,709 and 4,624,846. Antibodies against an antigen, e.g., a gastrointestinal, lung, breast, prostate, ovarian, testicular, brain or lymphatic tumor, a sarcoma or a melanoma, can be used.

A wide variety of monoclonal antibodies against infectious disease agents have been developed, and are summarized in a review by Polin, in Eur. J. Clin. Microbiol., 3(5): 387-398 (1984), showing ready availability. These include monoclonal antibodies (MAbs) against pathogens and their antigens such as the following: Anti-bacterial Mabs such as those against *Streptococcus agalactiae, Legionella pneumophilia, Streptococcus pyogenes, Esherichia coli, Neisseria gonorrhosae, Neisseria meningitidis, Pneumococcus, Hemophilis influenzae* B, *Treponema pallidum*, Lyme disease, *spirochetes, Pseudomonas aeruginosa, Mycobacterium leprae, Brucella abortus, Mycobacterium tuberculosis*, Tetanus toxin, Anti-protozoan Mabs such as those against *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Mesocestoides corti, Emeria tenella, Onchocerca volvulus, Leishmania tropica, Trichinella spiralis, Theileria parva, Taenia hydatigena, Taenia ovis, Taenia saginata*, Anti-viral MAbs such as those against HIV-1, -2, and -3, Hepatitis A, B, C, D, Rabies virus, Influenza virus, Cytomegalovirus, Herpes simplex I and II, Human serum parvo-like virus, Respiratory syncytial virus, Varicella-Zoster virus, Hepatitis B virus, Measles virus, Adenovirus, Human T-cell leukemia viruses, Epstein-Barr virus, Mumps virus, Sindbis virus, Mouse mammary tumor virus, Feline leukemia virus, Lymphocytic choriomeningitis virus, Wart virus, Blue tongue virus, Sendai virus, Reo virus, Polio virus, Dengue virus, Rubella virus, Murine leukemia virus, Antimycoplasmal MAbs such as those against *Acholeplasma laidlawii, Mycoplasma arthritidis, M. hyorhinis, M. orale, M. arginini, M. pneumonia*; etc.

Suitable MAbs have been developed against most of the micro-organisms (bacteria, viruses, protozoa, other parasites) responsible for the majority of infections in humans, and many have been used previously for in vitro diagnostic purposes. These antibodies, and newer MAbs that can be generated by conventional methods, are appropriate for use as target agents with the compounds provided herein.

MAbs against malaria parasites can be directed against the sporozoite, merozoite, schizont and gametocyte stages. Monoclonal antibodies have been generated against sporozoites (circumsporozoite antigen), and have been shown to neutralize sporozoites in vitro and in rodents (N. Yoshida et al., Science 207: 71-73 (1980)). Monoclonal antibodies to T. gondii, the protozoan parasite involved in toxoplasmosis have been developed (Kasper et al., J. Immunol. 129: 1694-1699 (1982). MAbs have been developed against schistosomular surface antigens and have been found to act against schistosomulae in vivo or in vitro (Simpson et al., Parasitology 83: 163-177 (1981); Smith et al., Parasitology 84: 83-91 (1982); Gryzch et al., J. Immunol. 129: 2739-2743 (1982); Zodda et al., J. Immunol. 129: 2326-2328 (1982); Dissous et al., J. Immunol. 129: 2232-2234 (1982).

It should be noted that mixtures of antibodies and immunoglobulin classes can be used, as can hybrid antibodies. Multispecific, including bispecific and hybrid, antibodies and antibody fragments are especially preferred in the methods of the present invention for detecting and treating target tissue and are comprised of at least two different substantially monospecific antibodies or antibody fragments, wherein at least two of said antibodies or antibody fragments specifically bind to at least two different antigens produced or associated with the targeted lesion or at least two different epitopes or molecules of a marker substance produced or associated with the target tissue. Multispecific antibodies and antibody fragments with dual specificities can be prepared analogously to the anti-tumor marker hybrids disclosed in U.S. Pat. No. 4,361,544. Other techniques for preparing hybrid antibodies are disclosed in, e.g., U.S. Pat. Nos. 4,474,893 and 4,479,895, and in Milstein et al., Immunol. Today 5: 299 (1984).

Antibody fragments useful in the present invention include F(ab')$_2$, F(ab)$_2$, Fab', Fab, Fv and the like including hybrid fragments. Preferred fragments are Fab', F(ab')$_2$, Fab, and F(ab)$_2$. Also useful are any subfragments retaining the hypervariable, antigen-binding region of an immunoglobulin and having a size similar to or smaller than a Fab' fragment. This will include genetically engineered and/or recombinant proteins, whether single-chain or multiple-chain, which incorporate an antigen-binding site and otherwise function in vivo as targeting vehicles in substantially the same way as natural immunoglobulin fragments. Such single-chain binding molecules are disclosed in U.S. Pat. No. 4,946,778, which is hereby incorporated by reference. Fab' antibody fragments may be conveniently made by reductive cleavage of F(ab')$_2$ fragments, which themselves may be made by pepsin digestion of intact immunoglobulin. Fab antibody fragments may be made by papain digestion of intact immunoglobulin, under reducing conditions, or by cleavage of F(ab)$_2$ fragments which result from careful papain digestion of whole immunoglobulin.

A ligand or one member of a ligand-receptor binding pair can be conjugated to the compounds provided herein for targeting the compounds to specific target tissues or target compositions. Examples of ligand-receptor binding pairs are set out in U.S. Pat. Nos. 4,374,925 and 3,817,837, the teachings of which are incorporated herein by reference.

Conjugation to ligands. Many compounds that can serve as targets for ligand-receptor binding pairs, and more specifically, antibodies, have been identified, and the techniques to construct conjugates of such ligands with photosensitizers are well known to those of ordinary skill in this art. For example, Rakestraw et al. teaches conjugating Sn(IV) chlorin e via covalent bonds to monoclonal antibodies using a modified dextran carrier (Rakestraw, S. L., Tompkins, R. D., and Yarmush, M. L., Proc. Nad. Acad. Sci. USA 87: 4217-4221 (1990). The compounds disclosed herein can also be conjugated to a ligand, such as an antibody, by using a coupling agent. Any bond which is capable of linking the components such that they are stable under physiological conditions for the time needed for administration and treatment is suitable, but covalent linkages are preferred. The link between two components may be direct, e.g., where a photosensitizer is linked directly to a targeting agent, or indirect, e.g., where a photosensitizer is linked to an intermediate and that intermediate being linked to the targeting agent.

A coupling agent should function under conditions of temperature, pH, salt, solvent system, and other reactants that substantially retain the chemical stability of the photosensitizer, the backbone (if present), and the targeting agent. Coupling agents should link component moieties stably, but such that there is only minimal or no denaturation or deactivation of the photosensitizer or the targeting agent. Many coupling agents react with an amine and a carboxylate, to form an amide, or an alcohol and a carboxylate to form an ester. Coupling agents are known in the art (see, e.g., M. Bodansky, "Principles of Peptide Synthesis", 2nd ed., and T. Greene and P. Wuts, "Protective Groups in Organic Synthesis," 2nd Ed, 1991, John Wiley, NY).

The conjugates of the compounds provided herein with ligands such as antibodies can be prepared by coupling the compound to targeting moieties by cleaving the ester on the "d" ring and coupling the compound via peptide linkages to the antibody through an N terminus, or by other methods known in the art. A variety of coupling agents, including cross-linking agents, can be used for covalent conjugation. Examples of cross-linking agents include N,N'-dicyclohexylcarbodiimide (DCC), N-succinimidyl-5-acetyl-thioacetate (SATA), N-succinimidyl-3-(2-pyridyidi-thio)propionate (SPDP), ortho-phenylene-dimaleimide (o-PDM), and sulfo-succinimidyl 4-(N-maleimido-methyl)-cyclohexane-1-carboxylate (sulfo-SMCC). See, e.g., Karpovsky et al. J. Exp. Med. 160:1686 (1984); and Liu, M A et al., Proc. Natl. Acad. Sci. USA 82: 8648 (1985). Other methods include those described by Brennan et al. Science 229: 81-83 (1985) and Glennie et al., J. Immunol. 139: 2367-2375 (1987). A large number of coupling agents for peptides and proteins, along with buffers, solvents, and methods of use, are described in the Pierce Chemical Co. catalog, pages O-90 to O-110 (1995, Pierce Chemical Co., 3747 N. Meridian Rd., Rockford Ill., 61105, U.S.A.), which catalog is hereby incorporated by reference.

For example, DCC is a useful coupling agent that can be used to promote coupling of the alcohol NHS to chlorin e6 in DMSO forming an activated ester which can be cross-linked to polylysine. DCC is a carboxy-reactive cross-linker commonly used as a coupling agent in peptide synthesis, and has a molecular weight of 206.32. Another useful cross-linking agent is SPDP, a heterobifunctional cross-linker for use with primary amines and sulfhydryl groups. SPDP has a molecular weight of 312.4, a spacer arm length of 6.8 angstroms, is reactive to NHS-esters and pyridyldithio groups, and produces cleavable cross-linking such that, upon further reaction, the agent is eliminated so the photosensitizer can be linked directly to a backbone or targeting agent. Other useful conjugating agents are SATA for introduction of blocked SH groups for two-step cross-linking, which is deblocked with hydroxylamine-HCl, and sulfo-SMCC, reactive towards amines and sulfhydryls. Other cross-linking and coupling agents are also available from Pierce Chemical Co. Additional compounds and processes, particularly those involving a Schiff base as an intermediate, for conjugation of proteins to other proteins or to other compositions, for example to reporter groups or to chelators for metal ion labeling of a protein, are disclosed in EPO 243,929 A2 (published Nov. 4, 1987).

Photosensitizers which contain carboxyl groups can be joined to lysine ϵ-amino groups in the target polypeptides either by preformed reactive esters (such as N-hydroxy succinimide ester) or esters conjugated in situ by a carbodiimide-mediated reaction. The same applies to photosensitizers which contain sulfonic acid groups, which can be transformed to sulfonyl chlorides which react with amino groups. Photosensitizers which have carboxyl groups can be joined to amino groups on the polypeptide by an in situ carbodiimide method. Photosensitizers can also be attached to hydroxyl groups, of serine or threonine residues or to sulfhydryl groups of cysteine residues.

Methods of joining components of a conjugate, e.g., coupling polyamino acid chains bearing photosensitizers to antibacterial polypeptides, can use heterobifunctional cross linking reagents. These agents bind a functional group in one chain and to a different functional group in the second chain. These functional groups typically are amino, carboxyl, sulfhydryl, and aldehyde. There are many permutations of appropriate moieties which will react with these groups and with differently formulated structures, to conjugate them together. See the Pierce Catalog, and Merrifield, R. B. et al., Ciba Found Symp. 186: 5-20 (1994).

The compounds or pharmaceutically acceptable derivatives thereof may be packaged as articles of manufacture containing packaging material, a compound or pharmaceutically acceptable derivative thereof provided herein, which is effective for modulating the activity of hyperproliferating tissue or neovascularization, or for treatment, prevention or amelioration of one or more symptoms of hyperproliferating tissue or neovascularization mediated diseases or disorders, or diseases or disorders in which hyperproliferating tissue or neovascularization activity, is implicated, within the packaging material, and a label that indicates that the compound or composition, or pharmaceutically acceptable derivative thereof, is used for modulating the activity of hyperproliferating tissue or neovascularization, or for treatment, prevention or amelioration of one or more symptoms of hyperproliferating tissue or neovascularization mediated diseases or disorders, or diseases or disorders in which hyperproliferating tissue or neovascularization is implicated.

The articles of manufacture provided herein contain packaging materials. Packaging materials for use in packaging pharmaceutical products are well known to those of skill in the art. See, e.g., U.S. Pat. Nos. 5,323,907; 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder in which hyperproliferating tissue or neovascularization is implicated as a mediator or contributor to the symptoms or cause.

3. Methods of Use.

A. Methods of PDT, Diagnostic and Therapeutic Applications. Briefly, the photosensitizing compound is generally administered to the subject before the target tissue, target composition or subject is subjected to illumination. The photosensitizing compound is administered as described elsewhere herein.

The dose of photosensitizing compound can be determined clinically. Depending on the photosensitizing compound used, an equivalent optimal therapeutic level will have to be established. A certain length of time is allowed to pass for the circulating or locally delivered photosensitizer to be taken up by the target tissue. The unbound photosensitizer is cleared from the circulation during this waiting period, or additional time can optionally be provided for clearing of the unbound compound from non-target tissue. The waiting period will be determined clinically and may vary from compound to compound.

At the conclusion of this waiting period, a laser light source or a non-laser light source (including but not limited to artificial light sources such as fluorescent or incandescent light, or natural light sources such as ambient sunlight) is used to activate the bound drug. The area of illumination is determined by the location and dimension of the pathologic region to be detected, diagnosed or treated. The duration of illumination period will depend on whether detection or treatment is being performed, and can be determined empirically. A total or cumulative period of time anywhere from between about 4 minutes and 72 hours can be used. In one embodiment, the illumination period is between about 60 minutes and 148 hours. In another embodiment, the illumination period is between about 2 hours and 24 hours.

Preferably, the total fluence or energy of the light used for irradiating, as measured in Joules, is between about 10 Joules and about 25,000 Joules; more preferably, between about 100 Joules and about 20,000 Joules; and most preferably, between about 500 Joules and about 10,000 Joules. Light of a wavelength and fluence sufficient to produce the desired effect is selected, whether for detection by fluorescence or for therapeutic treatment to destroy or impair a target tissue or target composition. Light having a wavelength corresponding at least in part with the characteristic light absorption wavelength of the photosensitizing agent is preferably used for irradiating the target issue.

The intensity or power of the light used is measured in watts, with each Joule equal to one watt-sec. Therefore, the intensity of the light used for irradiating in the present invention may be substantially less than 500 mW/cm$^2$. Since the total fluence or amount of energy of the light in Joules is divided by the duration of total exposure time in seconds, the longer the amount of time the target is exposed to the irradiation, the greater the amount of total energy or fluence may be used without increasing the amount of the intensity of the light used. The present invention employs an amount of total fluence of irradiation that is sufficiently high to activate the photosensitizing agent.

In one embodiment of using compounds disclosed herein for photodynamic therapy, the compounds are injected into the mammal, e.g. human, to be diagnosed or treated. The level of injection is usually between about 0.1 and about 0.5 mmol/kg of body weight. In the case of treatment, the area to be treated is exposed to light at the desired wavelength and energy, e.g. from about 10 to 200 J/cm$^2$. In the case of detection, fluorescence is determined upon exposure to light at a wavelength sufficient to cause the compound to fluoresce at a wavelength different than that used to illuminate the compound. The energy used in detection is sufficient to cause fluorescence and is usually significantly lower than is required for treatment.

Any one of the photosensitizing compounds disclosed herein or a pharmaceutically acceptable derivative thereof may be supplied in a kit along with instructions on conducting any of the methods disclosed herein. Instructions may be in any tangible form, such as printed paper, a computer disk that instructs a person how to conduct the method, a video cassette containing instructions on how to conduct the method, or a computer memory that receives data from a remote location and illustrates or otherwise provides the instructions to a person (such as over the Internet). A person may be instructed in how to use the kit using any of the instructions above or by receiving instructions in a classroom or in the course of treating a patient using any of the methods disclosed herein, for example.

Additional examples and specific examples of methods of using compounds and compositions of the present invention include but are not limited to the following:

(i) Treatment of opportunistic infections. Compounds, compositions and methods of the invention are useful for PDT of opportunistic infections, particularly of soft tissue. For antimicrobial treatment (via PDT) of infections, particularly wound infections, the infecting organism can include (as non limiting examples) *Staphylococcus aureus, Pseudomonas aeruginosa, Escherichia coli*. In nosocomial infections, *P. aeruginosa* is responsible for 8% of surgical-wound infections and 10% of bloodstream infections. In some embodiments the subjects are immunocompromised subjects, such as those afflicted with AIDS or undergoing treatment with immunosupressive agents.

(ii) Treatment of burns. Infections by *S. aureus* and gram-positive bacteria in general are particularly pronounced in burns (Lambrechts, 2005). The multidrug resistance of *S. aureus* presents significant medical challenges. In this regard, compounds, compositions and methods of the invention are useful for the treatment of opportunistic infections of burns.

(iii) Sepsis. Compounds, compositions and methods of the invention are useful for the PDT treatment of subjects afflicted with opportunistic infections of *Vibrio vulnificus. V. vulnificus*, a gram-negative bacterium, causes primary sepsis, wound infections, and gastrointestinal illness in humans.

(iv) Ulcers. Compounds, compositions and methods of the invention are useful for PDT treatment of the bacterium that causes ulcers (*Helicobacter pylori*). In the clinic, treatment can be effected in any suitable manner, such as by insertion of a fiber optic cable (akin to an endoscope but with provisions for delivery of red or near-IR light) into the stomach or afflicted region.

(v) Periodontal disease. Compounds, compositions and methods of the invention are useful in PDT for the treatment of periodontal disease, including gingivitis. Periodontal disease is caused by the overgrowth of bacteria, such as the gram-negative anaerobe *Porphyromonas gingivalis*. As with many PDT treatments, targeting or solubilizing entities in conjunction with the photoactive species are essential for appropriate delivery of the photoactive species to the desired cells. The oral pathogens of interest for targeting include *Porphyromonas gingivalis, Actinobacillus actinomycetemcomitans, Bacteroidesforsythus, Campylobacter rectus, Eikenella corrodens, Fusobacterium nucleatum* subsp. *Polymorphum, Actinomyces viscosus*, and the streptococci. For such applications the compounds or compositions of the invention can be topically applied (e.g., as a mouthwash or rinse) and then light administered with an external device, in-the-mouth instrument, or combination thereof.

(vi) Atherosclerosis. Compounds, compositions and methods of the invention are useful in PDT to treat vulnerable atherosclerotic plaque. Without wishing to be bound to any particular theory, invading inflammatory macrophages are believed to secrete metalloproteinases that degrade a thin layer of collagen in the coronary arteries, resulting in thrombosis, which often is lethal (Demidova and Hamblin, 2004). Bacteriochlorins targeted to such inflammatory macrophages are useful for PDT of vulnerable plaque.

(vii) Cosmetic and dermatologic applications. Compounds, compositions and methods of the invention are useful in PDT to treat a wide range of cosmetic dermatological problems, such as hair removal, treatment of psoriasis, or removal of skin discoloration. Ruby lasers are currently used for hair removal; in many laser treatments melanin is the photosensitized chromophore. Such treatments work reasonably well for fair-skinned individuals with dark hair. Compounds, compositions and methods of the invention can be used as near-IR sensitizers for hair removal, which enables targeting a chromophore with a more specific and sharp absorption band.

(viii) Acne. Compounds, compositions and methods of the invention are useful in PDT to treat acne. Acne vulgaris is caused by *Propionibacterium acnes*, which infects the sebaceous gland; some 80% of young people are affected. Here again, the growing resistance of bacteria to antibiotic treatment is leading to an upsurge of acne that is difficult to treat. Current PDT treatments of acne typically rely on the addition of aminolevulinic acid, which in the hair follicle or sebaceous gland is converted to free base porphyrins. Compounds and compositions of the invention can be administered to subjects topically or parenterally (e.g., by subcutaneous injection) depending upon the particular condition.

(ix) Infectious diseases. Compounds, compositions and methods of the invention are useful in PDT to treat infectious diseases. For example, Cutaneous leishmaniasis and sub-cutaneous leishmaniasis, which occurs extensively in the Mediterranean and Mideast regions, is currently treated with arsenic-containing compounds. PDT has been used to reasonable effect recently, at least in one case, on a human patient. The use of compounds and compositions of the present invention are likewise useful, and potentially offer advantages such as ease of synthesis and better spectral absorption properties.

(x) Tissue sealants. Compounds, compositions and methods of the invention are useful in PDT as tissue sealants in subjects in need thereof. Light-activated tissue sealants are attractive for sealing wounds, bonding tissue, and closing defects in tissue There are many applications where sutures or staples are undesirable, and use of such mechanical methods of sealing often lead to infection and scarring.

(xi) Neoplastic disease. Compounds, compositions and methods of the invention are useful in PDT for treating neoplastic diseases or cancers, including skin cancer, lung cancer, colon cancer, breast cancer, prostate cancer, cervical cancer, ovarian cancer, basal cell carcinoma, leukemia, lymphoma, squamous cell carcinoma, melanoma, plaque-stage cutaneous T-cell lymphoma, and Kaposi sarcoma.

B. Imaging Enhancing Agents. In addition to PDT, the compositions provided herein can be used as imaging enhancing agents in diagnostic imaging techniques, or for the labeling of target tissues or target compositions for diagnostic radiology. In the modern medical field, there are a variety of treatments including magnetic resonance imaging (MRI) for the diagnosis of diseases. Detection of cancer in its early stages should improve the ability to cure eliminate the cancerous tissue. Early diagnosis of precancerous regions and minute cancer are important subject matters in modern cancer treatments. MRI has emerged as a powerful tool in clinical settings because it is noninvasive and yields an accurate volume rendering of the subject. The image is created by imposing one or more orthogonal magnetic field gradients upon the subject or specimen while exciting nuclear spins with radio frequency pulses as in a typical nuclear magnetic resonance (NMR) experiment. After collection of data with a variety of gradient fields, deconvolusion yields a one, two, or three dimensional image of the specimen/subject. Typically, the image is based on the NMR signal from the protons of water where the signal intensity in a given volume element is a function of the water concentration and relaxation times. Local variation in there parameters provide the vivid contrast observed in MR images.

MRI contrast agents act by increasing the rate of relaxation, thereby increasing the contrast between water molecules in the region where the imaging agent accretes and water molecules elsewhere in the body. However, the effect of the agent is to decrease both $T_1$ and $T_2$, the former resulting in greater contrast while the latter results in lesser contrast. Accordingly, the phenomenon is concentration-dependent, and there is normally an optimum concentration of a paramagnetic species for maximum efficacy. This optimal concentration will vary with the particular agent used, the locus of imaging, the mode of imaging, i.e., spin-echo, saturation-recovery, inversion-recovery and/or various other strongly $T_1$-dependent or $T_2$-dependent imaging techniques, and the composition of the medium in which the agent is dissolved or suspended. These factors, and their relative importance are known in the art. See, e.g., Pykett, Scientific American 246: 78 (1982); Runge et al., *Am. J. Radiol.* 141: 1209 (1983). When MRI contrast agents are used diagnostically, they are vascularly perfused, enhancing the contrast of blood vessels and reporting on organ lesions and infiltration. However, the labeling of specific tissues for diagnostic radiology remains a difficult challenge for MRI. Efforts to develop cell and tissue-specific MRI image enhancing agents by modifying existing immunological techniques has been the focus of much research in diagnostic radiology. For example, antibodies labeled with paramagnetic ions, generally the gadolinium chelate Gd-DTPA, have been generated and tested for their effects on MRI contrast of tumors and other tissues (U.S. Pat. No. 5,059,415). Unfortunately, the relaxivity of Gd bound to antibodies has been found to be only slightly better than that of unbound Gd-DTPA (Paajanen et al., Magn. Reson. Med 13: 38-43 (1990)).

MRI is generally used to detect $^1H$ nuclei in the living body. However, MRI is capable of detecting NMR spectrums of other nuclear species, including $^{13}C$, $^{15}N$, $^{31}P$, and $^{19}F$. The $^{19}F$ is not abundant in the living body. By incorporating isotopes useful in MRI, such as $^{13}C$, $^{15}N$, $^{31}P$, or $^{19}F$, and particularly $^{19}F$ in the compositions provided herein and administering to a subject, the compounds provided herein would accumulate in target tissue, and subsequent MR imaging would produce NMR data with enhanced signal from the targeted tissue or target compositions due to the presence of the accumulated compound with the MRI recognizable isotope, such as $^{19}F$. Thus, the disclosed compounds can be used as image enhancing agents and provide labeling of specific target tissues or target compositions for diagnostic radiology, including MRI.

C. Detecting Target Tissue or Target Compositions. In addition to PDT, the compositions provided herein can be used to detect target cells, target tissue, or target compositions in a subject. When the compounds provided herein are to be used for detection of target tissue or target composition, the compounds are introduced into the subject and sufficient time is allowed for the compounds to accumulate in the target tissue or to become associated with the target composition. The area of treatment is then irradiated, generally using light of an energy sufficient to cause fluorescence of the compound, and the energy used is usually significantly lower than is required for photodynamic therapy treatment. Fluorescence is determined upon exposure to light at the desired wavelength, and the amount of fluorescence can be correlated to the presence of the compound, qualitatively or quantitatively, by methods known in the art.

D. Diagnosing an Infecting Agent. The compositions provided herein can be used to diagnose the presence of an infecting agent, or the identity of an infecting agent in a subject. The compounds provided herein can be conjugated to one or more ligands specific for an infecting agent, such as an antibody or antibody fragment, that selectively associates with the infecting agent, and after allowing sufficient time for the targeted compound to associate with the infecting agent and to clear from non-target tissue, the compound can be visualized, such as by exposing to light of an energy sufficient to cause fluorescence of the compound, or by imaging using diagnostic radiology, including MRI. By way of example, any one of the compounds provided herein can be conjugated to an antibody that is targeted against a suitable *Helicobacter pylori* antigen, and formulated into a pharmaceutical preparation that, when introduced into a subject, releases the conjugated compound to a gastric mucus/epithelial layer where the bacterium is found. After sufficient time for the compound to selectively associate with the target infecting agent, and for any unbound compound to clear from non-target tissue, the subject can be examined to determine whether any *Helicobacter pylori* is present. This can be done by MRI to detect accumulated compound because of the presence of $^{19}F$ substituents, for example, or by irradiating the suspect target area with light of an energy sufficient to cause fluorescence of the compound, such as by using fiberoptics, and detecting any fluorescence of the targeted compound.

3. Solar Cells, Light Harvesting Rods and Light Harvesting Arrays.

Bacteriochlorins of Formula I herein may be used as chromophores (also referred to as photosensitizers or simply sensitizers) in solar cells, including but not limited to high surface area colloidal semiconductor film solar cells (Gratzel cells), as described in, for example, U.S. Pat. Nos. 5,441,827; 6,420,648; 6,933,436; 6,924,427; 6,913,713; 6,900,382; 6,858,158; and 6,706,963.

Bacteriochlorins of Formula I may be used as chromophores in the light harvesting rods described in U.S. Pat. Nos. 6,407,330 and 6,420,648 (incorporated herein by reference). The light harvesting rod may comprise one or more bacteriochlorins of Formula I coupled to one or two adjacent chromophores depending upon the position thereof in the light harvesting rod. Such light harvesting rods may be utilized to produce light harvesting arrays as described in U.S. Pat. No. 6,420,648 and solar cells as described in U.S. Pat. No. 6,407,330.

4. Flow Cytometry.

Flow cytometry is known and described in, for example, U.S. Pat. Nos. 5,167,926; 5,915,925; 6,248,590; 6,589,792; and 6,890,487. In some embodiments the particle being detected, such as a cell, is labelled with a luminescent compound such as a phosphor or fluorophore for detection. Labelling can be carried out by any suitable technique such as coupling the luminescent compound to another compound such as an antibody which in turn specifically binds to the particle or cell, by uptake or internalization of the luminescent compound into the cell or particle, by non-specific adsorption of the luminescent compound to the cell or particle, etc. The bacteriochlorins described herein are useful in flow cytometry as such luminescent compounds, which flow cytometry techniques (including fluorescent activated cell sorting or FACS) may be carried out in accordance with known techniques or variations thereof which will be apparent to those skilled in the art based upon the instant disclosure.

5. Information Storage Devices.

Bacteriochlorins of the invention are also useful immobilized to a substrate for making charge storage molecules and information storage devices containing the same, either individually or as linked polymers thereof, either optionally including additional compounds to add additional oxidation states. Such charge storage molecules and information storage devices are known and described in, for example, U.S. Pat. No. 6,208,553 to Gryko et al.; U.S. Pat. No. 6,381,169 to Bocian et al.; and U.S. Pat. No. 6,324,091 to Gryko et al. The bacteriochlorins of the invention may comprise a member of a sandwich coordination compound in the information storage molecule, such as described in U.S. Pat. No. 6,212,093 to Li et al. or U.S. Pat. No. 6,451,942 to Li et al.

The present invention is explained in greater detail in the following non-limiting Examples.

EXPERIMENTAL

The strong absorption by bacteriochlorins in the near-IR region makes these pigments especially attractive for a wide variety of applications in medicine, the life sciences, and materials chemistry. Such applications require simple synthetic methods that afford access to ample quantities of stable compounds. Specific attributes of the desired methodology include the ability (1) to construct a macrocycle that is locked at the bacteriochlorin reduction level, and (2) to exercise synthetic control over the pattern of substituents arrayed around the perimeter of the macrocycle. The former objective can be met through the use of a geminal dimethyl group in each of the two pyrroline rings. The latter objective can be met by using hydrodipyrrin precursors containing the desired pattern of substituents to be carried over to the target bacteriochlorin. The structure of a target bacteriochlorin core (lacking peripheral substituents other than the geminal dimethyl groups) is shown in Chart 3.

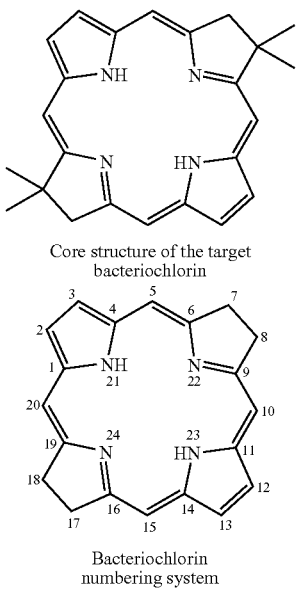

Chart 3

Core structure of the target bacteriochlorin

Bacteriochlorin numbering system

We here describe a de novo synthesis of bacteriochlorins where the bacteriochlorin reduction level is established by structural features in acyclic precursors to the macrocycle. The route that we developed draws on our prior work concerning the rational syntheses of chlorins (Strachan, J.-P. et al., J. Org. Chem. 2000, 65, 3160-3172; Strachan, J.-P. et al., J. Org. Chem. 2000, 65, 3160-3172) but also required extensive development. The route to bacteriochlorins employs the self-condensation of a dihydrodipyrrin-acetal wherein the pyrrolic end of the molecule functions as a nucleophile and the acetal functions as an electrophile. We describe the synthesis of the dihydrodipyrrin-acetal, a study of conditions for the self-condensation of the dihydrodipyrrin-acetal, and the characterization of the bacteriochlorins.

I. Experimental Section.

General. $^1$H NMR (400 MHz) and $^{13}$C NMR (100 MHz) spectra were collected at room temperature in $CDCl_3$. Absorption spectra were collected routinely. Melting points are uncorrected. Column chromatography was performed with flash silica or alumina (80-200 mesh). Bacteriochlorins were analyzed in neat form by laser desorption mass spectrometry (LD-MS) in the absence of a matrix. The $CHCl_3$ contained 0.8% ethanol.

Static Absorption and Emission. Static absorption and fluorescence measurements were performed as described previously (Li, F. et al., J. Mater. Chem. 1997, 7, 1245-1262; Strachan, J.-P. et al., J. Am. Chem. Soc. 1997, 119, 11191-11201; Yang, S. I. et al., J. Phys. Chem. B 1998, 102, 9426-9436). Non-deaerated samples with an absorbance $\leq 0.15$ at $\lambda_{exc}$ were used for the key emission measurements; the detection band-pass was 4-5 nm and the spectra were corrected for the detection-system spectral response.

Extinction Coefficients. The extinction coefficients of 12, 13, and In-12 were determined by dissolving a known quantity of each bacteriochlorin (~6 mg) in 100 mL of toluene. Then a known amount (~100 μL) of this solution was added to a quartz cuvette containing 3.0 mL of toluene. The absorption spectrum was recorded at room temperature.

Fluorescence Quantum Yields ($\Phi_f$). The $\Phi_f$ values were determined with bacteriochlorin samples where the $Q_x(0,0)$-band absorptions [511 (12) or 499 nm (13)] were ~0.08-0.1. The reference compound (t-Bu)$_4$H$_2$Pc, which emits in the region (~680-820) similar to that of the bacteriochlorins, was used as the standard ($\Phi_f$=0.77)(Teuchner, K. et al., Photochem. Photobiol 1993, 57, 465-471). The absorption (644 nm) of (t-Bu)$_4$H$_2$Pc was also between 0.08-0.1. Excitations were performed at 511 or 499 nm and the fluorescence emission spectra were obtained (600-900 nm) with correction for instrument response and temporal variation in light intensity. The spectra were then integrated from 600-900 nm, affording values for $I_{em}$. The $I_{em}$ values were divided by the absorption recorded at 511 or 499 nm respectively. Since the absolute $\Phi_f$ for (t-Bu)$_4$H$_2$Pc is known (0.77), the term $I_{em}/A_{644}$ obtained for (t-Bu)$_4$H$_2$Pc and for the bacteriochlorins can thus be used to calculate the relative $\Phi_f$ for the bacteriochlorins. All data were obtained in toluene at room temperature.

General procedure for investigation of conditions in bacteriochlorin forming reaction. The condensations were carried out in 1-dram vials containing magnetic stir bars. A freshly prepared sample of dihydrodipyrrin-acetal 11 (0.85-1.7 mg) was dissolved in a specific amount (0.50-2.0 mL) of a certain solvent. The condensation was initiated by adding the desired acid to the stirred reaction mixture at room temperature. The progress of the reaction was monitored by taking aliquots periodically from the reaction mixture via syringe and neutralizing with TEA, followed by absorption spectroscopy. In particular, for 5 mM reactions of 11, 10 μL aliquots were removed from the reaction vessel and diluted with 3 mL of $CH_2Cl_2$. The diluted solution was treated with one drop of TEA and the visible absorption spectrum was recorded. [In cases where the acid yielded a heterogeneous mixture (e.g., $InCl_3$, $Yb(OTf)_3$) or broadened absorption in the $Q_y$ region, the 10 μL aliquots were passed through a 2-cm long pipet column ($CH_2Cl_2$/ethyl acetate). The first collected sample (green; eluted with $CH_2Cl_2$) and the second collected sample (pink; eluted with ethyl acetate) were separately concentrated and then diluted with 3 mL of $CH_2Cl_2$. The visible absorption spectrum was recorded with the diluted solutions.] The yield of bacteriochlorins was determined by the intensity of the $Q_y$ band (above 700 nm, $\epsilon$=120,000 $M^{-1}$ $cm^{-1}$) measured from the apex to the middle point of base line, which lined from the blue edge to the red edge of the band. This eliminated the contribution of the other components, which may have absorption band in the region of above 700 nm.

In the case of insoluble acids, the dihydrodipyrrin-acetal 11 and the insoluble acids were pre-weighed in the vial followed by addition of a microstir bar. The reactions were initiated by addition of the desired solvent. The reactions were monitored as described above.

1,1-Dimethoxy-4-methyl-3-penten-2-one (2). A mixture of mesityl oxide (1) (18.0 mL, 160 mmol), diphenyl diselenide (5.00 g, 16.0 mmol), and ammonium peroxydisulfate (109 g, 480 mmol) in anhydrous MeOH (1.20 L) was refluxed for 4 h under argon. The progress of the reaction was monitored by TLC. The reaction mixture was poured into water (1.20 L) and extracted with chloroform. The organic layer was washed with water, dried ($Na_2SO_4$), and concentrated to give a dark brown oil. Bulb-to-bulb distillation of the oil at 50° C./0.04-0.05 mmHg gave a yellow oil. The oil was chromatographed [silica, hexanes/ethyl acetate (3:1)] to give a pale yellow oil (7.37 g, 29%). Analytical data were consistent with the literature[12] for the title compound: $^1H$ NMR δ 1.96 (d, J=1.2 Hz, 3H), 2.21 (d, J=1.2 Hz, 3H), 3.42 (s, 6H), 4.49 (s, 1H), 6.36-6.38 (m, 1H); $^{13}C$ NMR δ 21.3, 28.2, 54.5, 104.5, 119.1, 160.2, 194.2; FAB-MS obsd 159.1020, calcd 159.1021 ($C_8H_{14}O_3$) $[M+H]^+$. Note: The use of reagent grade methanol resulted in a slow reaction (required >26 h for completion) versus the relatively fast reaction (<4 h) when anhydrous methanol was used.

In situ generation of mono-Ethyl malonate (4). A solution of ethyl malonate potassium salt (27.0 g, 158 mmol) in water (20.0 mL) was treated with concentrated HCl (~35%, 15.0 mL) and the resulting mixture was stirred for 10 min at room temperature. The mixture was extracted with ether. The extracts were washed with water, dried ($Na_2SO_4$), and concentrated to give a colorless oil (16.7 g, 79%). The oil was used for subsequent reaction without characterization.

Ethyl-3-(4-methylphenyl)prop-2-enoate (5). A solution of 3 (11.6 g, 96.9 mmol) and 4 (16.7 g, 126 mmol) in piperidine (958 μL, 9.69 mmol) and pyridine (39.2 mL, 485 mmol) was refluxed for 8 h under argon. The reaction mixture was cooled to room temperature and the reaction was quenched with 2 N HCl (~250 mL). The reaction mixture was extracted with ether. The extracts were washed with water, base ($NaHCO_3$), and water. The organic solution was dried ($Na_2SO_4$), concentrated, and chromatographed (silica, $CH_2Cl_2$) to give a colorless oil (14.6 g, 79%): $^1H$ NMR δ 1.33 (t, J=7.2 Hz, 3H), 2.37 (s, 3H), 4.26 (q, J=7.2 Hz, 2H), 6.39 (d, J=15.8 Hz, 1H), 7.18 (d, J=8.2 Hz, 2H), 7.42 (d, J=8.2 Hz, 2H), 7.66 (d, J=15.8 Hz, 1H); $^{13}C$ NMR δ 14.5 21.6, 60.6, 117.4, 128.2, 129.8, 131.9, 140.8, 144.8, 167.4; Anal. Calcd for $C_{12}H_{14}O_2$: C, 75.76; H, 7.42. Found: C, 75.76; H, 7.44.

3-(Ethoxycarbonyl)-4-(4-methylphenyl)pyrrole (6). A solution of TosMIC (15.7 g, 80.5 mmol) and 5 (14.6 g, 76.7 mmol) in a dry ether/DMSO (2:1) (154 mL) solution was added dropwise under argon to a stirred solution of NaH (2.39 g, 99.7 mmol) in ether (70 mL). The mixture started to reflux due to the exothermic reaction. After 3 h, water (200 mL) was carefully added to the mixture and the aqueous phase was extracted with ether and $CH_2Cl_2$. The combined organic extracts were dried ($Na_2SO_4$), concentrated, and chromatographed [silica, $CH_2Cl_2$/ethyl acetate (9:1)] to give a light brown solid (13.1 g, 74%): mp 154-155° C.; $^1H$ NMR δ 1.25 (t, J=7.2 Hz, 3H), 2.36 (s, 3H), 4.22 (q, J=7.2 Hz, 2H), 6.75-6.77 (m, 1H), 7.16 (d, J=7.8 Hz, 2H), 7.38 (d, J=7.8 Hz, 2H), 7.46-7.48 (m, 1H), 8.38-8.54 (br, 1H); $^{13}C$ NMR δ 14.5, 21.4, 59.8, 113.9, 118.3, 125.4, 126.8, 128.6, 129.4, 132.0, 136.3, 165.2; Anal. Calcd for $C_{14}H_{15}NO_2$: C, 73.34; H, 6.59; N, 6.11. Found: C, 73.11; H, 6.59; N, 6.12.

3-(4-Methylphenyl)pyrrole (7). Following a standard procedure (Balasubramanian, T. et al., J. Org. Chem. 2000, 65, 7919-7929), a mixture of 6 (6.81 g, 29.7 mmol) and ethylene glycol (76.0 mL) in a 250-mL Claisen flask was flushed with argon for 10 min, and then powdered NaOH (3.05 g, 76.2 mmol) was added. The flask was placed in an oil bath at 120° C. and the oil bath temperature was raised to 160° C. After 2.5 h, the flask was cooled to room temperature and 10% aqueous NaCl (150 mL) was added. The aqueous layer was extracted with $CH_2Cl_2$. The organic layers were collected, washed with 10% aqueous NaCl, dried ($Na_2SO_4$), concentrated, and chromatographed (silica, $CH_2Cl_2$) to give a light brown solid (3.33 g, 71%): mp 92-93° C.; $^1H$ NMR δ 2.34 (s, 3H), 6.51-6.54 (m, 1H), 6.82-6.84 (m, 1H), 7.05-7.08 (m, 1H), 7.15 (d, J=7.8 Hz, 2H), 7.43 (d, J=7.8 Hz, 2H), 8.15-8.32 (br, 1H); $^{13}C$ NMR δ 21.3, 106.7, 114.4, 119.0, 125.1, 125.4, 129.5, 133.1, 135.2; FAB-MS obsd 157.0885, calcd 157.0891 ($C_{11}H_{11}N$).

2-Formyl-3-(4-methylphenyl)pyrrole (8). Following a standard procedure (Balasubramanian, T. et al., J. Org. Chem. 2000, 65, 7919-7929), a solution of 7 (472 mg, 3.00 mmol) in DMF (0.96 mL) and $CH_2Cl_2$ (30 mL) under argon was cooled to 0° C. and then $POCl_3$ (340 μL, 3.60 mmol) was added dropwise. After 1 h, the flask was warmed to room temperature and stirred overnight (~18 h). The reaction was quenched at 0° C. with 2.5 M NaOH (25 mL). The mixture was poured into water (50 mL), extracted with $CH_2Cl_2$, and the combined organic layers were washed with water, brine, dried ($Na_2SO_4$), and concentrated. The residue was chromatographed [silica, $CH_2Cl_2$/ethyl acetate (9:1)] to give a brown solid. $^1H$ NMR spectroscopy showed two regioisomers in ~13:1 ratio. Cooling of the solution (ethyl acetate/hexanes) at ~−16° C. resulted in precipitation of an orange solid, which proved to be a single regioisomer (354 mg, 64%): mp 149-150° C.; $^1H$ NMR δ 2.41 (s, 3H), 6.42-6.44 (m, 1H), 7.10-7.13 (m, 1H), 7.26 (d, J=8.0 Hz, 2H), 7.40 (d, J=8.0 Hz, 2H), 9.63-9.64 (m, 1H), 9.52-9.78 (br, 1H); $^{13}C$ NMR δ 21.4, 111.6, 126.2, 128.9, 129.3, 129.7, 130.9, 137.7, 137.9, 180.2; FAB-MS obsd 186.0907, calcd 186.0919 ($C_{12}H_{11}NO$).

2-(2-Nitroethyl)-3-(4-methylphenyl)pyrrole (9). A mixture of 8 (3.93 g, 21.2 mmol), KOAc (2.29 g, 23.3 mmol), methylamine hydrochloride (1.72 g, 25.4 mmol), and nitromethane (190 mL) under argon was stirred at room temperature. The mixture slowly became orange and yielded an orange-red precipitate. After stirring for 2.5 h, TLC showed the appearance of a new component and the disappearance of 8. The reaction was quenched with brine, extracted with ethyl acetate, and the organic layers were dried ($Na_2SO_4$) and concentrated. The residue was dissolved in THF/MeOH (210 mL, 3:7) at 0° C. $NaBH_4$ (2.41 g, 63.6 mmol) was added in portions at 0° C. Then the mixture was stirred for 0.5 h at room temperature. The reaction mixture was neutralized with acetic acid (pH=7), then water (150 mL) was added and the mixture was extracted with ethyl acetate. The combined organic layers were washed with water, brine, dried (Na$_2$SO$_4$), concentrated, and chromatographed [silica, hexanes/ethyl acetate (3:1)] to give a light brown solid (3.61 g, 74%): mp 81-82° C.; $^1$H NMR δ 2.37 (s, 3H), 3.44 (t, J=6.8 Hz, 2H), 4.54 (t, J=6.8 Hz, 2H), 6.27-6.29 (m, 1H), 6.73-6.75 (m, 1H), 7.20 (d, J=8.2 Hz, 2H), 7.23 (d, J=8.2 Hz, 2H), 8.19-8.36 (br, 1H); $^{13}$C NMR δ 21.2, 24.4, 75.2, 109.6, 117.7, 121.9, 123.2, 128.0, 129.5, 133.4, 135.8; FAB-MS obsd 230.1055, calcd 230.1055 (C$_{13}$H$_{14}$N$_2$O$_2$).

6-[3-(4-Methylphenyl)pyrrol-2-yl]-1,1-dimethoxy-4,4-dimethyl-5-nitro-2-hexanone (10). Following a general procedure (Strachan, J.-P et al., supra; Balasubramanian, T et al., supra), CsF (1.82 g, 12.0 mmol, 3.00 mol equiv, freshly dried by heating to 100° C. under vacuum for 1 h and then cooling to room temperature under argon) was placed in a flask under argon. A mixture of 9 (921 mg, 4.00 mmol) and acetal 2 (6.33 g, 40.0 mmol, 10 mol equiv) in dry acetonitrile (40 mL) was transferred by cannula to the flask containing CsF. The mixture was heated at 65° C. for 1.2 h, whereupon TLC analysis showed the reaction to be complete. The reaction mixture was filtered through a bed of silica (ethyl acetate) and the filtrate was concentrated. The resulting oil was subjected to bulb-to-bulb distillation at room temperature/0.04-0.05 mmHg for 3 h, affording recovery of the acetal 2 (~2 g) as the distillate and the desired product in the crude undistilled residue. Purification of the residue by column chromatography [alumina, ethyl acetate/hexanes (1:3)] gave a light brown solid (626 mg, 40%): mp 98-100° C.; $^1$H NMR δ 1.09 (s, 3H), 1.19 (s, 3H), 2.37 (s, 3H), 2.53, 2.71 (AB, $^2$J=18.8 Hz, 2H), 3.21 (ABX, $^3$J=2.4 Hz, $^2$J=15.4 Hz, 1H), 3.39 (ABX, $^3$J=11.6 Hz, $^2$J=15.4 Hz, 1H), 3.41 (s, 6H), 4.34 (s, 1H), 5.22 (ABX, $^3$J=2.4 Hz, $^3$J=11.6 Hz, 1H), 6.22-6.24 (m, 1H), 6.66-6.68 (m, 1H), 7.19 (d, J=8.0 Hz, 2H), 7.24 (d, J=8.0 Hz, 2H), 8.06-8.14 (br, 1H); $^{13}$C NMR δ 21.3, 24.1, 24.3, 25.3, 36.8, 45.1, 55.2, 55.2, 95.0, 104.7, 109.5, 117.7, 122.1, 123.7, 128.4, 129.4, 133.5, 135.6, 203.7; Anal. Calcd for C$_{21}$H$_{28}$N$_2$O$_5$: C, 64.93; H, 7.27; N, 7.21. Found: C, 65.02; H, 7.34; N, 7.14.

1-(1,1-Dimethoxymethyl)-3,3-dimethyl-7-(4-methylphenyl)-2,3-dihydrodipyrrin (11). Following the procedure for preparing a β-substituted pyrrole, a solution of 10 (237 mg, 0.610 mmol) in anhydrous THF (3.00 mL) under argon was treated with NaOMe (165 mg, 3.05 mmol) and the mixture was stirred for 1 h at room temperature (first flask). In a second flask, TiCl$_3$ (8.6 wt % TiCl$_3$ in 28 wt % HCl, 4.56 mL, 3.05 mmol, 5.0 mol equiv) and H$_2$O (24 mL) were combined; NH$_4$OAc (18.8 g, 244 mmol) was added to buffer the solution to pH 6.0; and then THF (1.60 mL) was added. The solution in the first flask containing the nitronate anion of 10 was transferred via a cannula to the buffered TiCl$_3$ solution in the second flask. The resulting mixture was stirred at room temperature for 6 h under argon. Then the mixture was extracted with ethyl acetate. The combined organic layers were washed with 5% aqueous NaHCO$_3$ and water, and then dried (NaSO$_4$). The solvent was removed under reduced pressure at room temperature. The crude product was passed through a short column [alumina, hexanes/ethyl acetate (2:1)] to afford a light yellow solid (57 mg, 28%): mp 104-105° C.; $^1$H NMR δ 1.19 (s, 6H), 2.38 (s, 3H), 2.62 (s, 2H), 3.45 (s, 6H), 5.03 (s, 1H), 6.11 (s, 1H), 6.28-6.30 (m, 1H), 6.86-6.88 (m, 1H), 7.22 (d, J=8.0 Hz, 2H), 7.35 (d, J=8.0 Hz, 2H), 10.80-10.90 (br, 1H); $^{13}$C NMR δ 21.3, 29.3, 40.5, 48.3, 54.8, 103.0, 106.2, 109.3, 119.2, 124.7, 126.9, 128.7, 129.4, 134.2, 135.4, 160.1, 174.2; FAB-MS obsd 338.2020, calcd 338.1994; Anal. Calcd for C$_{21}$H$_{26}$N$_2$O$_2$: C, 74.52; H, 7.74; N, 8.28. Found: C, 74.46; H, 7.79; N, 8.08; λ$_{abs}$ (CH$_2$Cl$_2$) 358.

7,8,17,18-Tetrahydro-5-methoxy-8,8,18,18-tetramethyl-2,12-bis(4-methlyphenyl)porphyrin (12). A solution of 11 (93 mg, 0.27 mmol) in CH$_3$CN (54 mL) was treated with neat BF$_3$.OEt$_2$ (350 μL, 2.7 mmol, 50 mM). The reaction mixture was stirred at room temperature for 15 h. The reaction was monitored by absorption spectroscopy. TEA (1.0 mL) was added to the reaction mixture. The reaction mixture was concentrated and the residue was dissolved in CH$_2$Cl$_2$. The solution was washed (water), dried (Na$_2$SO$_4$), concentrated and chromatographed [silica, CH$_2$Cl$_2$/hexanes (1:1)]. The first band (green) was collected (13, 8.1 mg, 11%) and then the second band (green) was collected (12, 24 mg, 30%). Data for 12: $^1$H NMR δ −1.90 (br, 1H), −1.78 (br, 1H), 1.91 (s, 6H), 1.92 (s, 6H), 2.61 (s, 6H), 4.40 (s, 2H), 4.41 (s, 2H), 4.49 (s, 3H), 7.58 (d, J=8.0 Hz, 4H), 8.10 (d, J=8.0 Hz, 2H), 8.14 (d, J=8.0 Hz, 2H), 8.66-8.69 (m, 2H), 8.78 (s, 1H), 8.81 (s, 1H), 8.94-8.95 (m, 1H); λ$_{abs}$ (toluene)/nm 356 (ε=110,000), 374 (130,000), 511 (39,000), 732 (120,000 M$^{-1}$ cm$^{-1}$); LD-MS obsd 580.1; FAB-MS obsd 580.3232, calcd 580.3202 (C$_{39}$H$_{40}$N$_4$O).

Data for 13: $^1$H NMR δ −2.00 (br, 2H), 1.93 (s, 12H), 2.61 (s, 6H), 4.56 (s, 4H), 7.59 (d, J=8.0 Hz, 4H), 8.13 (d, J=8.0 Hz, 4H), 8.73 (d, J=2.0 Hz, 2H), 8.81 (s, 2H), 8.86 (s, 2H); λ$_{abs}$ (toluene)/nm 351 (ε=130,000), 374 (120,000), 499 (35,000), 737 (130,000 M$^{-1}$ cm$^{-1}$); LD-MS obsd 550.0; FAB-MS obsd 550.3068, calcd 550.3096 (C$_{38}$H$_{38}$N$_4$).

II. Results and Discussion

Strategy. During the course of the development of a de novo synthesis of bacteriochlorins, we examined the reactivity of a number of hydrodipyrrins each containing one pyrrole and one pyrroline unit. We eventually found that a dihydrodipyrrin (A) bearing a dimethyl acetal moiety attached to the carbon of the pyrroline imine unit underwent self-condensation to give bacteriochlorins (Scheme 1).

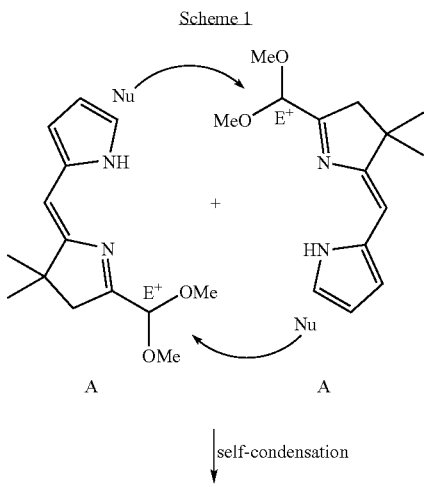

Scheme 1

-continued

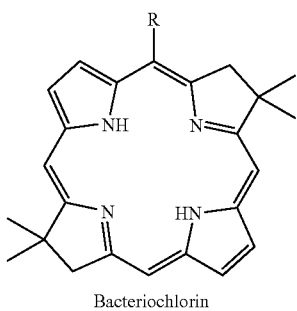

Bacteriochlorin

R = H, OMe

This result validated the approach of employing pyrrole/pyrroline moieties to serve as complementary nucleophilic/electrophilic counterparts. However, a number of problems with the condensation were immediately evident, including the very low yield (~1%) and the formation of a mixture of bacteriochlorins. We decided to build on this result to develop a more reliable synthesis.

The initial target molecules of choice were hydrodipyrrin-carboxaldehydes rather than the acetal A. The hydrodipyrrin-carboxaldehydes B and C differ only in the presence or absence of an unsaturation at the 4,5-position (between the meso-carbon and the pyrroline α'-carbon). (Chart 4).

Chart 4

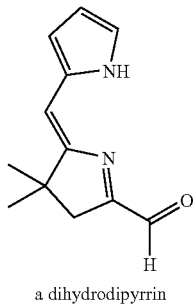

a dihydrodipyrrin

B

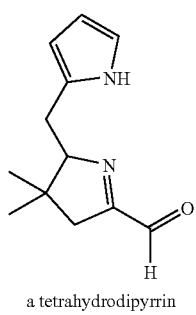

a tetrahydrodipyrrin

C

However, we were unable to prepare either B or C. Two observations from the literature concerning related structures (Chart 5) prompted the next step in the evolution of the synthesis.

Chart 5

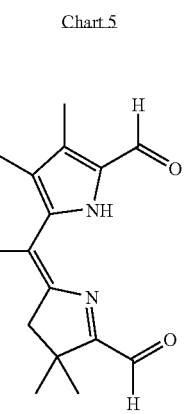

D

R:

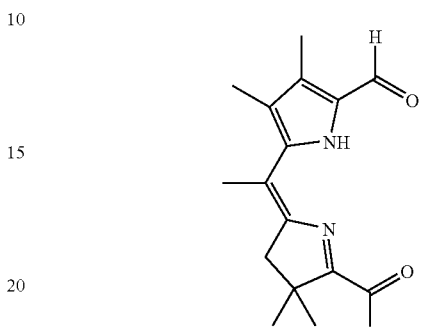

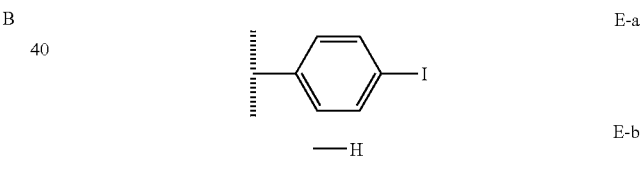

E-a

E-b

First, Jacobi et al. developed a rational route to chlorins (Jacobi, P. A. et al., Org. Lett. 2001, 3, 831-834) wherein a diformyl-dihydrodipyrrin (D) was employed. The dihydrodipyrrin bears the desired formyl group at the α-position of the pyrroline group, while also incorporating a nearly full complement of substituents throughout the molecule. Second, dihydrodipyrrins bearing an aryl substituent in the β-position (E-a) of the pyrrole ring are known to be more stable than unsubstituted analogs (E-b). Accordingly, we focused on the development of a route that would employ a β-pyrrole substituted dihydrodipyrrin analog (11) of the tetrahydrodipyrrin-acetal A. The p-tolyl group was chosen as an inert substituent that is readily characterized by $^1$H NMR spectroscopy.

Synthesis of Bacteriochlorin Precursors. The synthesis of dihydrodipyrrin-acetal 11 was initiated in similar fashion to a prior synthesis of a dihydrodipyrrin bearing a substituent at the β-position of the pyrrole ring (E-a).

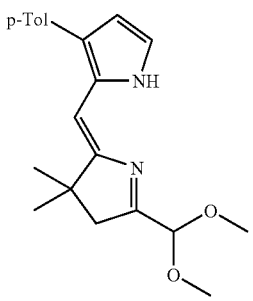

One of the key components in the synthesis of 11 is an α-keto acetal (2). Tiecco et al. reported the facile synthesis of α-keto acetals from ketones, including α-keto acetal 2,[12] albeit at a small scale. An excess amount of the α,β-unsaturated ketone (~5-10 equiv) has typically been employed in Michael additions with a nitroethyl pyrrole. Thus, we applied the method of Tiecco (Tiecco, M. et al., *J. Org. Chem.* 1990, 55, 4523-4528) using a catalytic amount of diphenyl diselenide and excess ammonium peroxydisulfate at much larger scale (160 mmol versus 2 mmol) to prepare α-keto acetal 2. Bulb-to-bulb distillation afforded a product that showed unidentified impurities in the $^1$H NMR spectrum. Subsequent chromatography gave pure α-keto acetal 2 (~7 g) in 29% yield (Scheme 2).

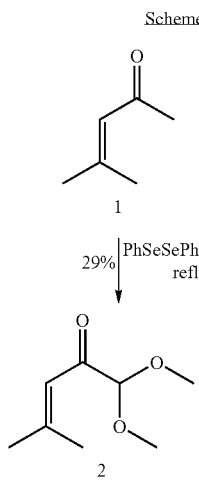

Application of the previously unused Knoevenagel condensation (Silva, N. M. et al., *Eur. J. Med. Chem.* 2002, 37, 163-170; Diaz, J. L. et al., *Chem. Mater.* 2002, 14, 2240-2251; Ren, X. et al., *Tetrahedron: Asymmetry* 2002, 13, 1799-1804) of p-tolualdehyde with malonic acid monoethyl ester (Breslow, D. S. et al., *J. Am. Chem. Soc.* 1944, 66, 1286-1288) in pyridine containing a catalytic amount of piperidine gave the known α,β-unsaturated ethyl cinnamate 5 (Tsuge, O. et al., *J. Org. Chem.* 1982, 47, 5171-5177; Colas, C.; Goeldner, M. *Eur. J. Org. Chem.* 1999, 1357-1366; Chuzel, O.; Piva, O. *Synth. Commun.* 2003, 33, 393-402) in 79% yield. Reaction of 5 with (p-tolylsulfonyl)methyl isocyanide (TosMIC) afforded β-substituted pyrrole 6 (a known compound with incomplete data (Di Santo, R. et al., *Med. Chem. Res.* 1997, 7, 98-108)) in 74% yield. Removal of the ethoxycarbonyl group of pyrrole 6 by treatment with NaOH in ethylene glycol at 160° C. gave the known β-substituted pyrrole 7 (Sakai, K. et al., *Chem. Pharm. Bull.* 1980, 28, 2384-2393; Campi, E. M. et al., *Aust. J. Chem.* 1992, 45, 1167-1178; Pavri, N, P.; Trudell, M. L. *J. Org. Chem.* 1997, 62, 2649-2651) in 71% yield. Vilsmeier-Haack formylation of 7 yielded a mixture of regioisomers owing to substitution at the 2- or 5-position. After column chromatography, the two regioisomers were determined to be present in ~13:1 ratio by $^1$H NMR integration of the methyl unit of the p-tolyl group. Selective precipitation readily afforded the major regioisomer 8 in 64% yield (Scheme 3).

It is noteworthy that we previously employed the same formylation method to prepare 2-formyl-3-(4-iodophenyl) pyrrole, which was characterized by $^1$H NMR spectroscopy and X-ray crystallography (Balasubramanian, T. et al., *J. Org Chem.* 2000, 65, 7919-7929).[E1] The chemical shift of the two peaks (δ 6.42-6.44 and 7.10-7.13 ppm) from the pyrrolic protons of the major isomer 8 were quite similar to those for 2-formyl-3-(4-iodophenyl)pyrrole (δ 6.42 and 7.14 ppm) and 2-formyl-3-phenylpyrrole (δ 6.50 and 7.30 ppm) (Cue, B. W. et al., *J. Heterocycl. Chem.* 1981, 18, 667-670). The minor isomers, 2-formyl-4-(4-methylphenyl)pyrrole (δ 7.20-7.22 and 7.36-7.38 ppm) and 2-formyl-4-(4-iodophenyl)pyrrole (δ 7.21 and 7.39 ppm), also showed similar chemical shifts for the respective pyrrolic protons.

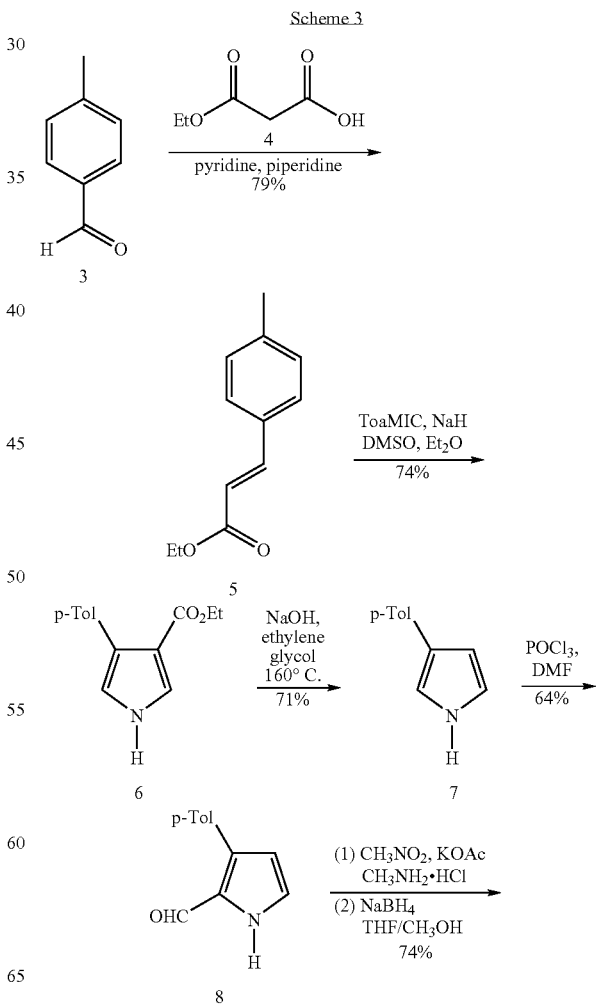

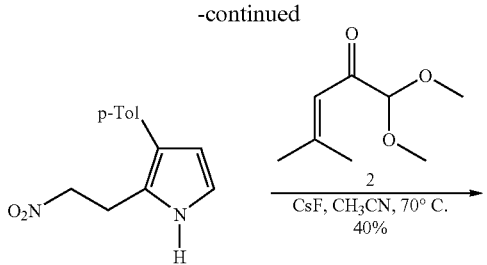

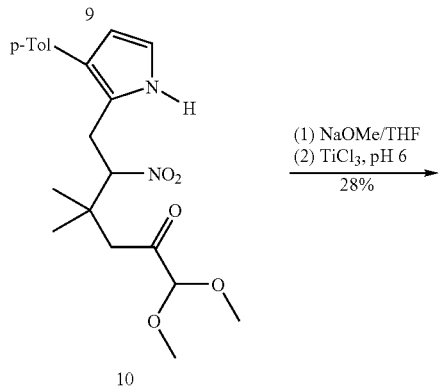

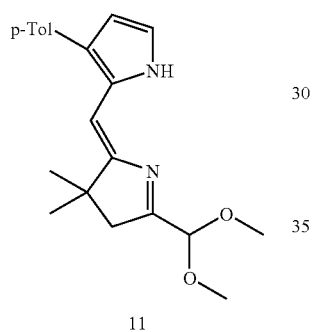

Treatment of 8 to the standard conditions for nitro-aldol condensation with pyrrole-2-carboxaldehyde (KOAc and a slight excess of methylamine hydrochloride in nitromethane at room temperature) for 2.5 h afforded the crude nitrovinyl pyrrole as a brown solid. Reduction of the latter with NaBH₄ gave the β-substituted nitroethylpyrrole 9 (74% for this two-step one-flask synthesis). The reaction of 9 with excess α-keto acetal 2 (10 equiv) in the presence of CsF at 65° C. gave 10 in 40% yield, accompanied by recovery of acetal 2 (~50%) upon bulb-to-bulb distillation and column chromatography. Treatment of 10 with NaOMe followed by a buffered TiCl₃ solution afforded the dihydrodiyrrin-acetal 11 as a yellow solid in 28% yield.

Investigation of Reaction Conditions for Bacteriochlorin Formation. A series of microscale studies (~1-2 mg of 11 per reaction) was performed to investigate effects of reaction parameters that are known to influence the course of condensations leading to porphyrinic macrocycles, including concentration of 11, acid composition, acid concentration, solvent, and time. The standard conditions employed initially included 5 mM of acetal 11 in CH₃CN containing 50 mM of acid at room temperature, which closely resemble those in the self-condensation of the unsubstituted dihydrodipyrrin-acetal A. Samples were removed periodically over the course of 24 h, neutralized with TEA, and examined by absorption spectroscopy. Yields were calculated on the basis of the assumption that each bacteriochlorin has $\epsilon_{Qy}$=120,000 M$^{-1}$ cm$^{-1}$, an assumption that proved valid (vide infra).

A. Acids. A screening study was performed to identify the effects of a variety of acids on the self-condensation of 11. Four Brønsted acids and eleven Lewis acids were examined. The acids can be categorized on the basis of bacteriochlorin yields: BF₃.OEt₂ (31%); InCl₃, Sc(OTf)₃, or SnCl₄ (18-16%); p-TsOH.H₂O (4.9%); Yb(OTf)₃, SnF₄, TiCl₄, BBr₃, or HCl (1.5-0.4%), and AcOH, TFA, MgBr₂, ZnCl₂, or Zn(OAc)₂ (~0%). The acids InCl₃ and Yb(OTf)₃ gave a slightly different reaction course, affording a free base bacteriochlorin, a metalated bacteriochlorin, and a non-bacteriochlorin macrocycle. This work will be described elsewhere.

B. Solvents. The effect of solvent on the self-condensation of 11 was examined with BF₃.OEt₂ catalysis under the standard conditions. The bacteriochlorin yields were ~30% (CH₃CN), <2% (CHCl₃ or ClCH₂CH₂Cl), and not detectable (CH₂Cl₂, toluene, DMF, DMSO, THF, 1,4-dioxane, methanol, ethanol).

The reaction with BF₃.OEt₂ catalysis was scaled up. The reaction of 11 (5 mM) with BF₃.OEt₂ (50 mM) in CH₃CN at room temperature proceeded smoothly and was complete in ~5-6 h. Two bacteriochlorins [12 (30%), 13 (11%)] were readily separated upon silica chromatography. Analysis by ¹H NMR spectroscopy showed that 12 has a methoxy group in a meso position of the macrocycle whereas 13 is unsubstituted (Scheme 4). Each bacteriochlorin was characterized by ¹H NMR, LD-MS, absorption spectra, and high resolution mass spectrometry (vide infra). The dramatic increase in yield (versus the <1% yield with the unsubstituted dihydrodipyrrin-acetal A) validated our hunch that β-substitution would afford a more stable substrate and more efficient reaction.

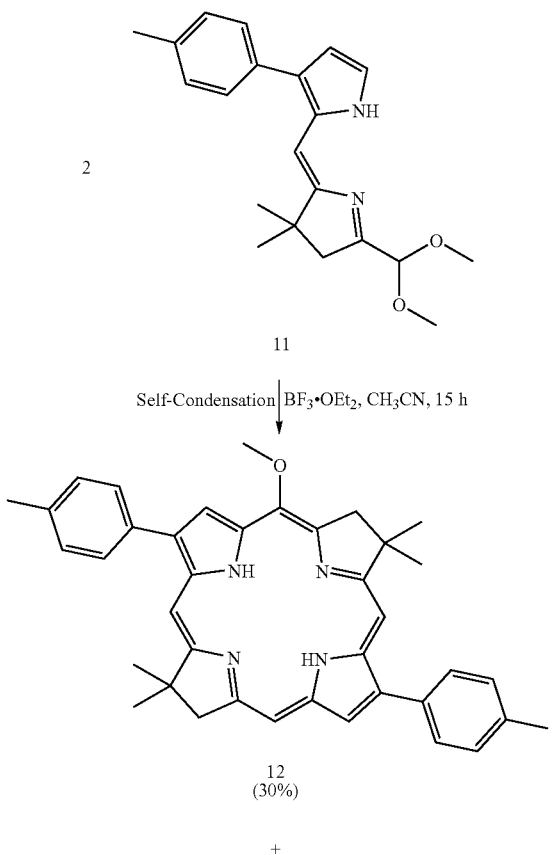

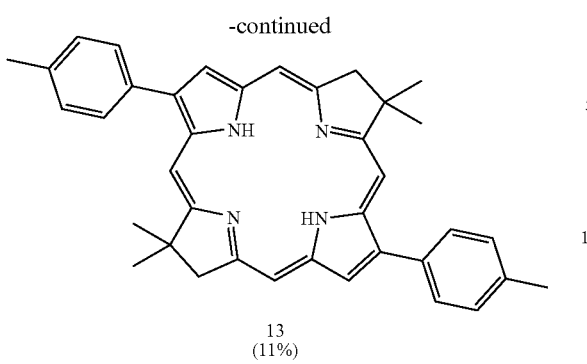

13
(11%)

Figure 2:
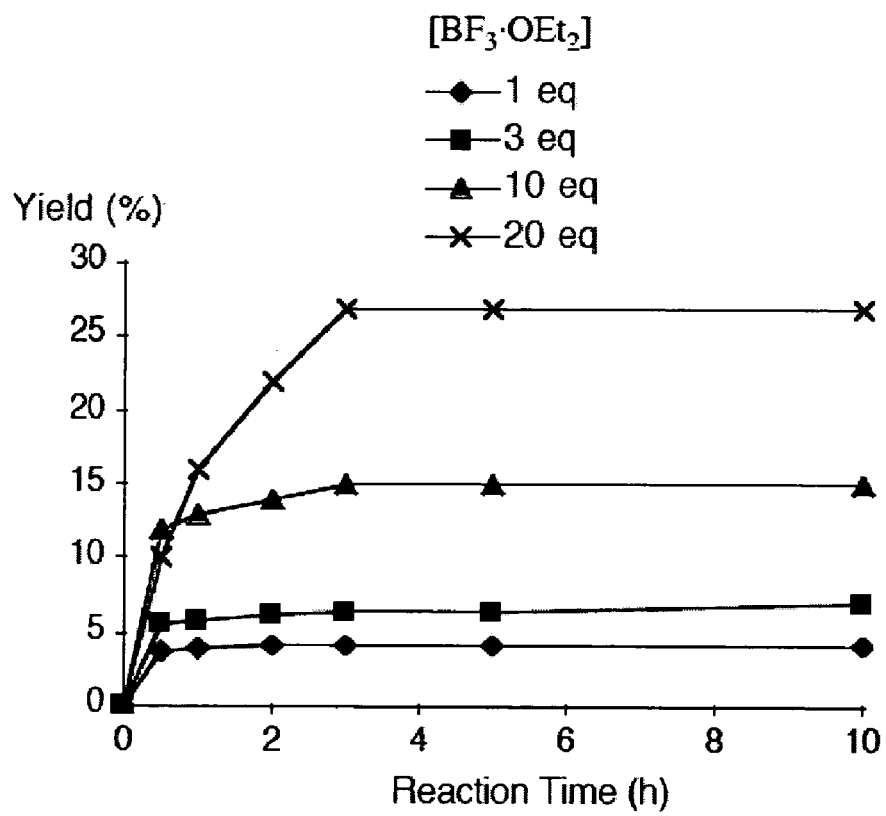
FIG. 2. The effect of the different concentrations of $BF_3 \cdot OEt_2$ in bacteriochlorin formation (12+13). The reaction was carried out with 5 mM of dihydrodipyrrin-acetal 11 in $CH_3CN$ at room temperature. The yield was determined by absorption spectroscopy in $CH_2Cl_2$.

C. Acid Concentration. The effect of $BF_3.OEt_2$ concentration on the self-condensation of 11 was examined next. Under the standard condition (5 mM of dihydrodipyrrin-acetal 11 in $CH_3CN$), the concentration of $BF_3.OEt_2$ was examined over the range of 1-20 equivalents (i.e., 5-100 mM). The yields of bacteriochlorins (sum of 12+13) are shown in FIG. 2. The reaction yields were quite dependent on the amount of acid used. The condensation of dihydrodipyrrin-acetal 11 generally proceeded well with >10 equiv of acid, while 20 equiv of $BF_3.OEt_2$ gave the highest overall yield of the two bacteriochlorins.

Some information also was obtained concerning the ratio of products (12:13) as a function of acid concentration. For example when less than 10 equiv of $BF_3$ $OEt_2$ was used, the major product was 12, whereas 20 equiv of $BF_3.OEt_2$ gave 13 as a major product. The ratio of 12 to 13 was not determined because the respective absorption spectra are nearly identical, differing only by ~10 nm in the $Q_x$ bands [12 (511 μm), 13 (499 nm)].

Figure 3:
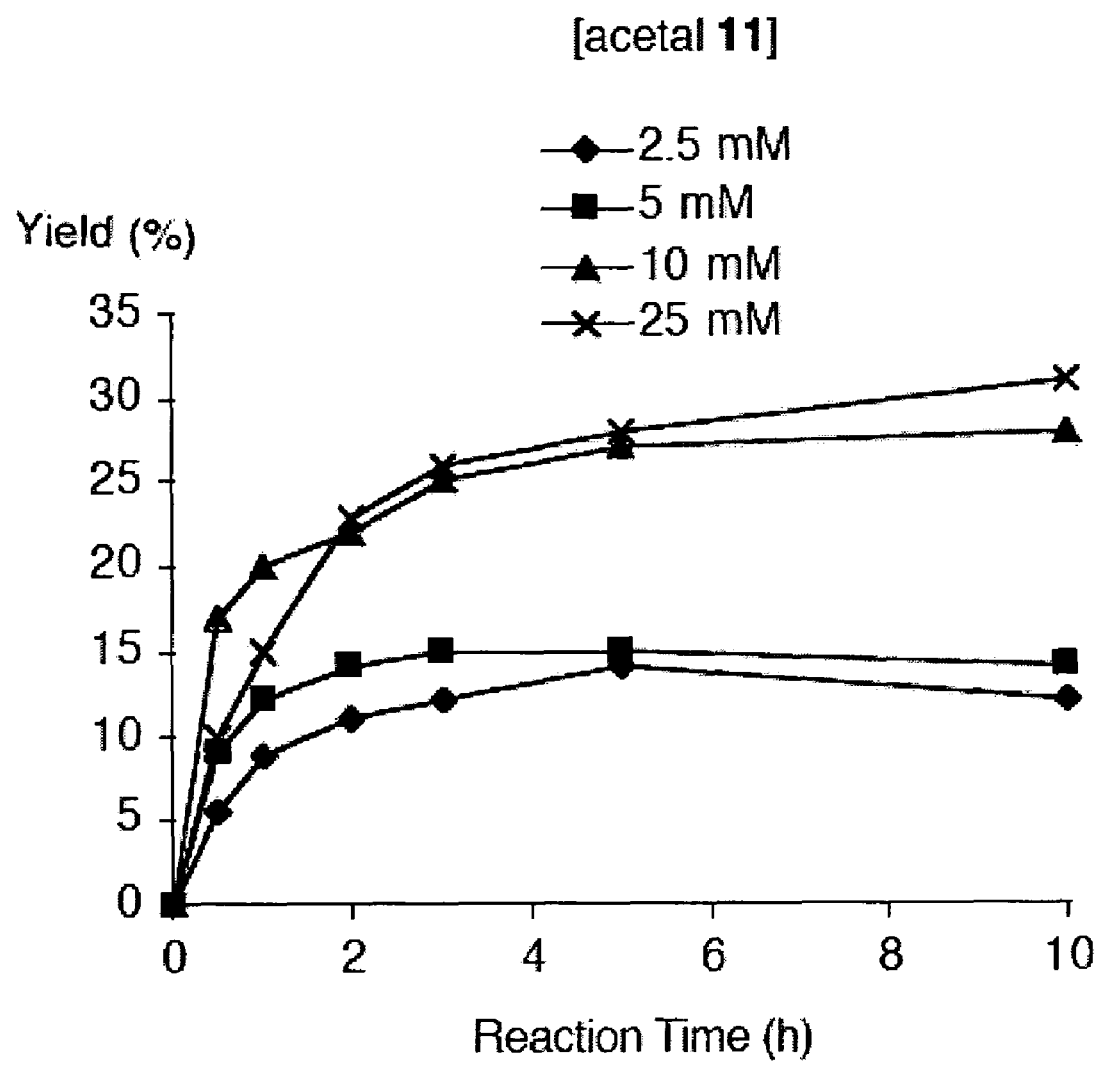
FIG. 3. The effect of different concentrations of dihydrodipyrrin-acetal 11 on bacteriochlorin formation (12+13). The reaction was carried out with $BF_3 \cdot OEt_2$ (10 equiv) in $CH_3CN$ at room temperature. The yield was determined by absorption spectroscopy in $CH_2Cl_2$.

D. Concentration. The effect of different concentrations also was examined. The concentration of dihydrodipyrrin-acetal 11 was examined over the range 2.5-25 mM in $CH_3CN$ with a constant 1:10 ratio of concentrations of 11 and $BF_3.OEt_2$ (i.e., the $BF_3.OEt_2$ concentration was scaled from 25-250 mM). In general, higher concentrations afforded higher yields of product. A further facet was that reaction at 10 mM gave 12 as a major product whereas that at 25 mM gave 13 as a major product (FIG. 3).

Bacteriochlorin Formation. The studies described led to the following reaction conditions. The reaction with dihydrodipyrrin-acetal 11 (5 mM) in $CH_3CN$ containing $BF_3.OEt_2$ (50 mM) at room temperature gave two separable bacteriochlorins (12 and 13) in ~40% overall yield (Scheme 4). The typical ratio of 12 and 13 was ~3:1. Upon reaction at higher concentrations of 11 (25 mM) and $BF_3.OEt_2$ (250 mM), 13 was the major product with the total yield of both bacteriochlorins remaining ~40%. These results show that the ratio of 12 and 13 can be influenced by the $BF_3.OEt_2$ concentration and the concentration of the dihydrodipyrrin-acetal 11.

The synthetic bacteriochlorins (12 and 13) are extraordinarily robust. For example, the bacteriochlorins are stable upon standing on the bench top in solution open to air for more than 10 days, as well as chromatography on silica in air in the presence of bright ambient lighting. Unlike bacteriochlorins derived from photosynthetic bacteria, the synthetic bacteriochlorins do not undergo adventitious dehydrogenation upon routine handling.

Mechanistic Considerations. At present we know very little about the mechanistic course leading from the dihydrodipyrrin-acetal to the bacteriochlorin species. The balanced reaction for formation each bacteriochlorin product (lacking aryl substituents for simplicity) is shown in Scheme 5.

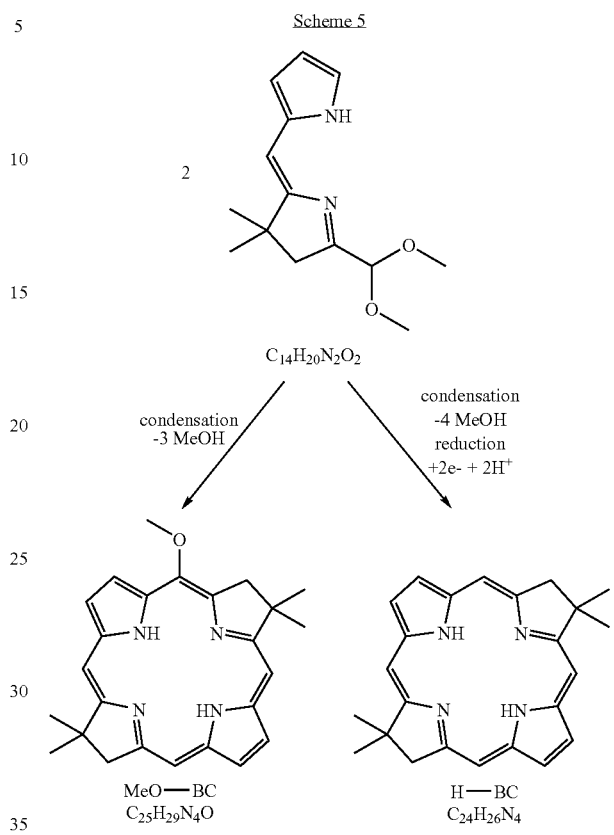

The conversion of two molecules of the dihydrodipyrrin-acetal (DHDPA, analogous to 11) to give the 5-methoxybacteriochlorin (MeO-BC) must proceed with elimination of three molecules of methanol. By contrast, the formation of the unsubstituted bacteriochlorin (H-BC) must proceed with elimination of four molecules of methanol and addition of 2e– and $2H^+$. Neither the source of the reductant nor the nature of the intermediate that undergoes reduction is known. It is worthwhile to contrast this overall transformation with that of porphyrin formation from an aldehyde and pyrrole, which proceeds via condensation to give a hexahydroporphyrin (porphyrinogeni) intermediate, which then is converted via a $6e–/6H^+$ oxidation to give the porphyrin (Lindsey, J. S. In *The Porphyrin Handbook*, Kadish, K. M., Smith, K. M., Guilard, R., Eds.; Academic Press: San Diego, Calif., 2000; Vol. 1, pp 45-118). Bacteriochlorin formation from the dihydrodipyrrin-acetal does not require an oxidant. Further consideration of oxidation-state changes is likely to be important in searching for intermediates and in designing alternative precursors to give bacteriochlorins.

Figures 1, 4:
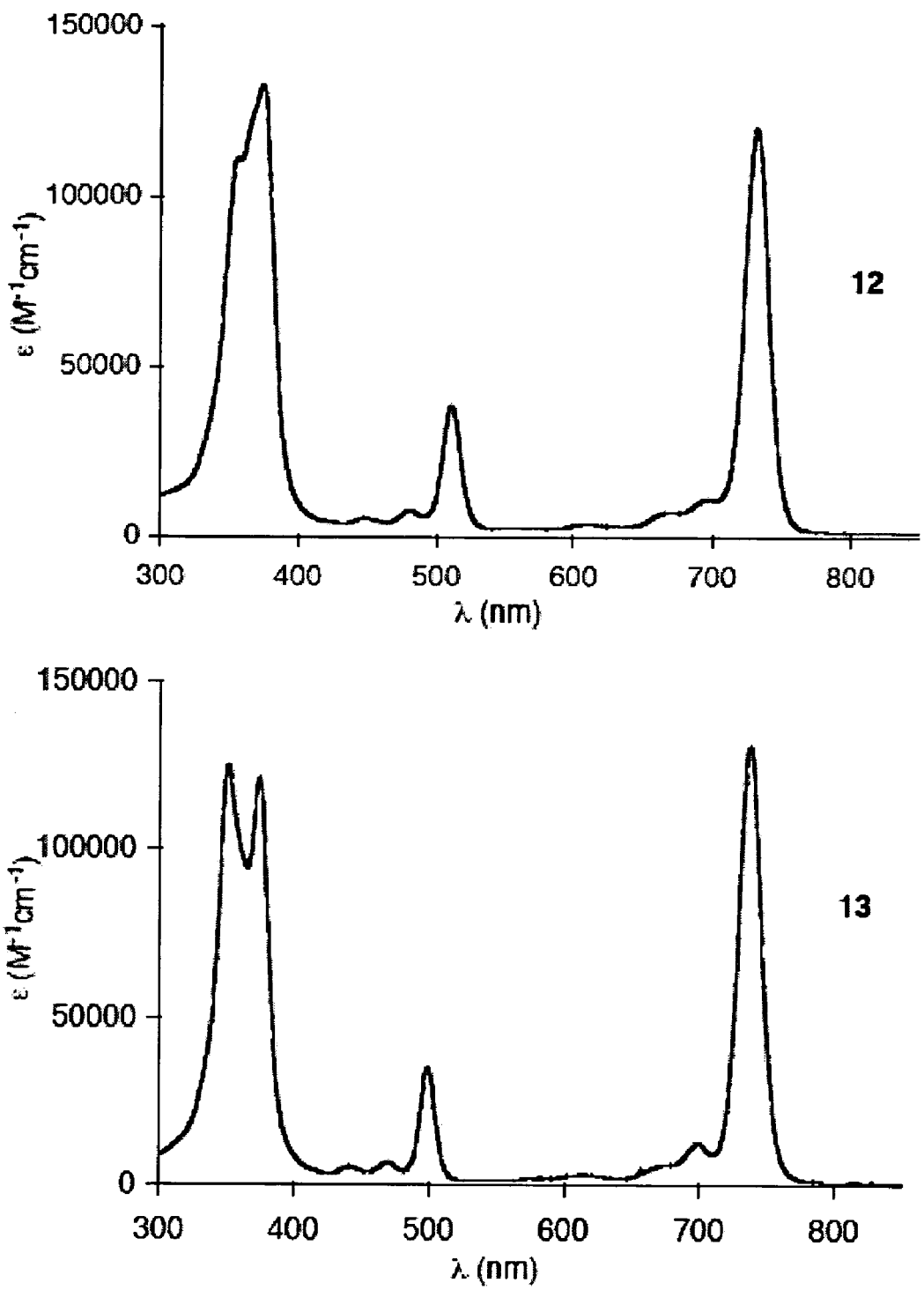
FIG. 4. Absorption and emission spectra in toluene at room temperature of 12 and 13.
Figures 2, 4:
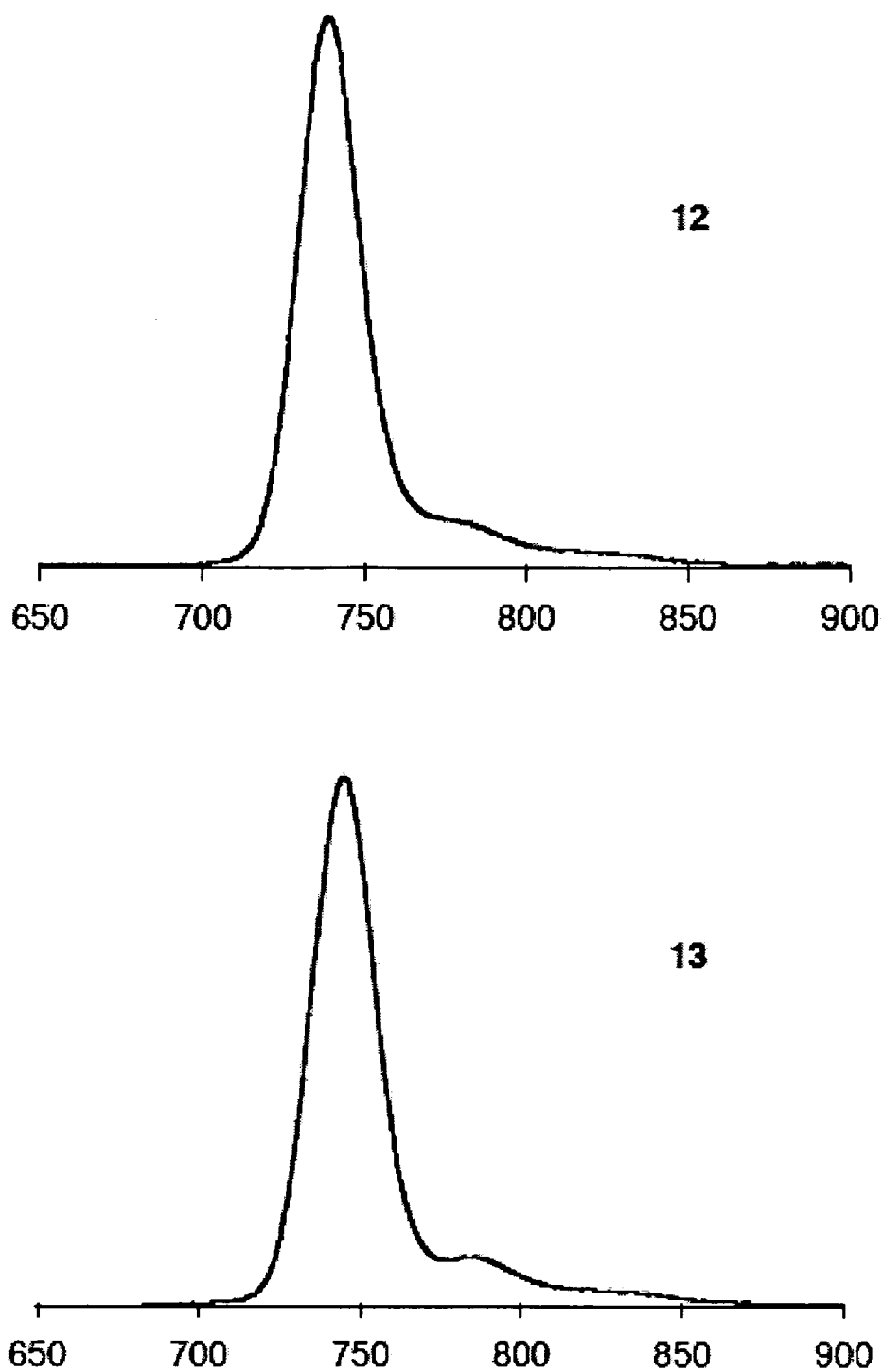

Characterization of the Bacteriochlorins. Absorption Spectra. The absorption spectra of 12 and 13 in toluene are shown in FIG. 4-1. Free base bacteriochlorin 12 exhibits broadened Soret bands with a single peak at 356 nm and a single peak at 374 nm. A weak $Q_x(0,0)$ band and a strong $Q_y(0,0)$ band appear at 511 and 732 nm, respectively. Free base bacteriochlorin 13 exhibits two Soret bands ($B_y$, $B_x$) at 351 and 374 nm. A weak $Q_x(0,0)$ band and a strong $Q_y(0,0)$ band appear at 499 and 737 nm, respectively. The absorption spectrum of free base tetraphenylbacteriochlorin ($H_2TPBC$, $\lambda_{abs}$ 356, 378, 520, and 742 nm) in benzene is very close to that of free base bacteriochlorins 12 and 13. The overall spectral features and band intensities of the bacteriochlorins prepared herein resemble those of bacteriochlorophyll a as well as those of synthetic bacteriochlorins (Fajer, J. et al., *Proc. Natl. Acad. Sci. USA.* 1974, 71, 994-998; Hartwich, G. et al., *J. Am. Chem. Soc.* 1998, 120, 3675-3683; Whitlock, H. W. et al., *J. Am. Chem. Soc.* 1969, 91, 7485-7489; Dorough, G. D.; Miller, J. R. *J. Am. Chem. Soc.* 1952, 74, 6106-6108; Dorough, G. D.; Huennekens, F. M. *J. Am. Chem. Soc.* 1952, 74, 3974-3976; Miller, J. R.; Dorough, G. D. *J. Am. Chem. Soc.* 1952, 74, 3977-3981). The bacteriochlorins exhibit a light green appearance in dilute solution in $CH_2Cl_2$ or toluene.

Fluorescence Properties. The fluorescence spectra and fluorescence quantum yields of 12 and 13 were collected in toluene at room temperature. The fluorescence spectrum of each bacteriochlorin is dominated by a $Q_y(0,0)$ band with Stokes shift of ~7-9 nm (FIG. 4-2). The wavelength of the $Q_y(0,0)$ emission maximum and fluorescence quantum yield ($\Phi_f$) are given in Table 1. Measurements of the fluorescence quantum yield ($\Phi_f$) of the bacteriochlorins using $(t\text{-}Bu)_4H_2Pc$ ($\Phi_f$=0.77) (Teuchner, K. et al., *Photochem. Photobiol.* 1993, 57, 465-471) as a reference gave values of 0.21 and 0.22 for 12 and 13, respectively.

Very few data are available concerning the fluorescence quantum yields ($\Phi_f$) of bacteriochlorins. The free base analog of the naturally occurring bacteriochlorophyll a (bacteriopheophytin a) has $\Phi_f$ estimated to be 0.12, (Connolly, J. S. et al., *Photochem. Photobiol.* 1982, 36, 565-574) whereas bacteriochlorin derivatives of $13^1$-deoxo-20-formyl-pyropheophorbide exhibited very low $\Phi_f$ values (~0.002) (Pandey, R. K. et al., *J. Med. Chem.* 1997, 17, 2770-2779). Synthetic bacteriochlorins such as meso-tetrakis(3-hydroxyphenyl)bacteriochlorin (Bonnett, R. et al., *J. Chem. Soc. Perkin Trans.* 2 1999, 325-328) or 5,15-diphenylbacteriochlorin (Wang, T. Y. et al., *Dyes and Pigments* 2002, 52, 199-208) gave $\Phi_f$ values of 0.11 or 0.14, respectively. On the other hand, the dioxobacteriochlorin derived from octaethylporphyrin was reported to have $\Phi_f$ of 0.48. The dearth of fundamental information concerning the fluorescence properties of bacteriochlorins must stem in large part to the prior lack of synthetic accessibility.

Laser Desorption Mass Spectrometry (LD-MS). Porphyrins typically give a strong molecule ion peak upon laser-desorption mass spectrometry (LD-MS) without requirement for use of a matrix.[H8] LD-MS analysis of 12 or 13 gave the molecule ion peak (m/z=580.1 or 550.0), consistent with the proposed structures (Scheme 4). The mass difference (~30) between 12 and 13 is consistent with the presence of the methoxy group in the former compound.

$^1$H NMR Spectra. The $^1$H NMR spectra of 12 and 13 are readily assignable. In the case of 13, which has Ch symmetry, a relatively simple $^1$H NMR spectrum is observed. A broad upfield peak (δ –1.96 ppm), singlet at δ 1.93 ppm, and singlet at δ 4.46 ppm are attributed to the two NH protons, the pair of geminal dimethyl groups, and the $CH_2$ groups of the pyrroline rings, respectively. The aryl hydrogens of the p-tolyl groups give a characteristic pair of doublets (J=8.0 Hz) at δ 7.59 ppm and 8.13 ppm. A doublet (J=2.0 Hz) at δ 8.73 ppm and two singlets at δ 8.81 and 8.86 ppm stem from the six protons (3, 5, 10, 13, 15, and 20 positions) about the perimeter of the bacteriochlorin.

Bacteriochlorin 12 has generally similar features, but the presence of the 5-methoxy group results in $C_s$ symmetry. Accordingly, the two NH protons (δ –1.90 and –1.78 ppm), the two pairs of geminal dimethyl groups (δ 1.91 and 1.92 ppm), and the two methylene units in each of the reduced pyrrole rings (δ 4.40 and 4.41 ppm) are non-equivalent and appear as distinct singlets. Each p-tolyl group gives a pair of doublets (J=8.0, 8.4 Hz in each case) in the region of δ 7.56-7.59 ppm and 8.09-8.15 ppm. The five peripheral protons (3, 10, 13, 15, and 20 positions) give rise to apparent singlets (δ 8.68, 8.78, and 8.81 ppm), a doublet (δ 8.94 ppm), and a partially overlapping peak at δ 8.67 ppm. Taken together, the absorption, LD-MS, and $^1$H NMR spectroscopic data support the structures proposed for bacteriochlorins 12 and 13.

Conclusions. A straightforward 8-step synthesis has been developed that affords free base bacteriochlorins. Each bacteriochlorin bears two geminal dimethyl groups to lock in the bacteriochlorin hydrogenation level, two β-substituents, and zero (13) or one (12) methoxy group in a meso position. The self-condensation of dihydrodipyrrin-acetal 11 proceeds under mild acid catalysis at room temperature without requirement for an oxidant and affords the free base bacteriochlorins in ~40% yield (12+13). Workable quantities (10-100 mg) of the bacteriochlorins can be readily prepared. The bacteriochlorins exhibit characteristic absorption and fluorescence properties. The bacteriochlorins are resistant to dehydrogenation and are stable to a variety of reaction conditions. This approach should provide ready access to bacteriochlorins bearing a variety of substituents, an essential feature for fundamental studies and use in diverse applications.

EXAMPLE 2

Bacteriochlorins Via a Dihydrodipyrrin-Carboxaldehyde

Recently and as described above, we developed a concise synthetic route to stable bacteriochlorins (Kim, H.-J.; Lindsey, J. S. *J. Org. Chem.* 2005, 70, 5475-5486). The synthesis employs the self-condensation of a dihydrodipyrrin-acetal. Here we describe a new synthetic route to bacteriochlorins. The new route involves oxidation of a dihydrodipyrrin to give the corresponding dihydrodipyrrin-aldehyde, which undergoes self-condensation to give free base bacteriochlorins (H-BC and an unidentified-BC) and a tetradehydrocorrin-aldehyde. The new route can be used as an alternative route for bacteriochlorin synthesis. Use of the aldehyde rather than the acetal affords a number of advantages.

Results and Discussion

1. Approach. In our previous work, we prepared a number of hydrodipyrrins and examined the reactivity of those hydrodipyrrins to find synthetic routes to stable bacteriochlorins. Three prototypical target hydrodipyrrin structures are shown in Chart 6.

Chart 6

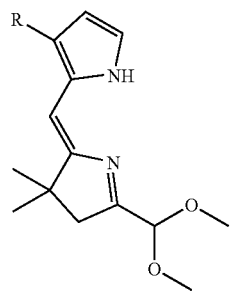

A

-continued

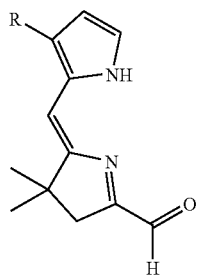

B

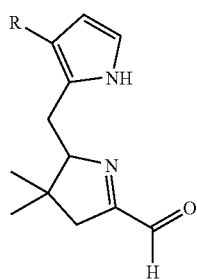

C

Each hydrodipyrrin contains a pyrrole ring and a pyrroline ring. We were able to prepare A but were not able to obtain B and C. We eventually found that dihydrodipyrrin-acetal A underwent self-condensation to give bacteriochlorins. Indeed, when R is a p-tolyl group, the dihydrodipyrrin-acetal (1) gives two bacteriochlorins (H-BC, MeO-BC) and a tetradehydrocorrin (TDC). The yield of each macrocycle was reasonable (yields of 30-49% for H-BC and MeO-BC and 66% for TDC; optimized for the respective macrocycle) and can be controlled by the reaction conditions. The three macrocycles are shown in Scheme 6.

Scheme 6

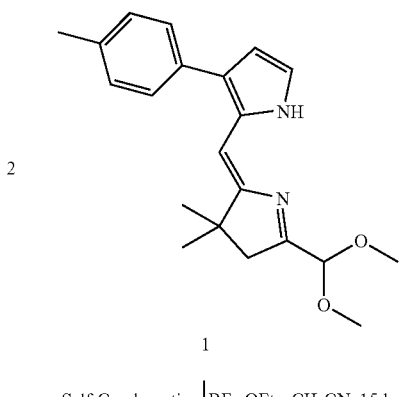

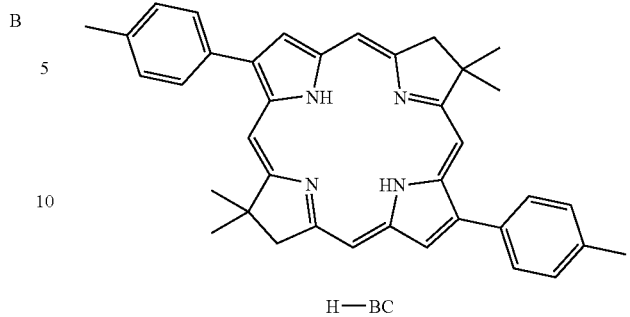

H—BC

+

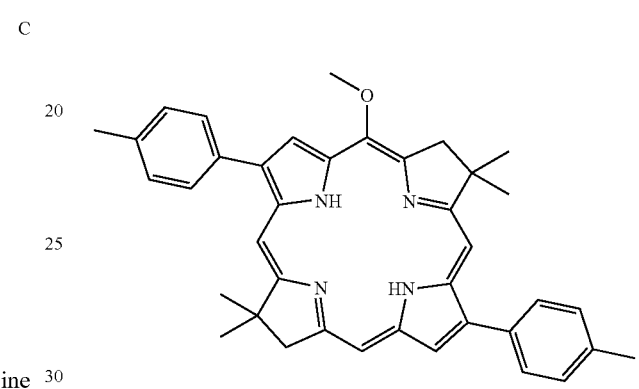

MeO—BC

+

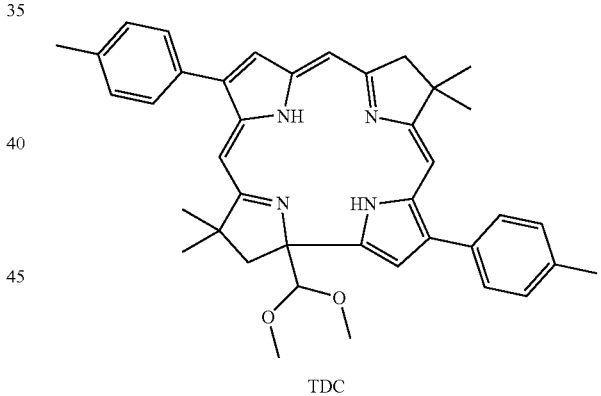

TDC

We are interested in achieving new route and better synthetic control of bacteriochlorin formation because the reaction gave three different macrocycles. Moreover, the reaction mechanism of self-condensation of the acetal is not clear. We turned to two new targets, aldehyde derivatives of a dihydrodipyrrin or a tetrahydrodipyrrin (B and C); such intermediates may furnish a superior synthetic method and also facilitate probing the bacteriochlorin-forming process. However, we were unable to prepare either B or C previously.

The new synthetic route to the targets B and C is summarized in Scheme 7. Routes to both derivatives were inspired by the work of Jacobi et al (*Org. Lett.* 2001, 3, 831-834). They converted the α-methyl group of a pyrroline unit to the formyl group via oxidation with $SeO_2$. Accordingly, we focused on the synthesis of dihydrodipyrrin-aldehyde derivatives and their self-condensation.

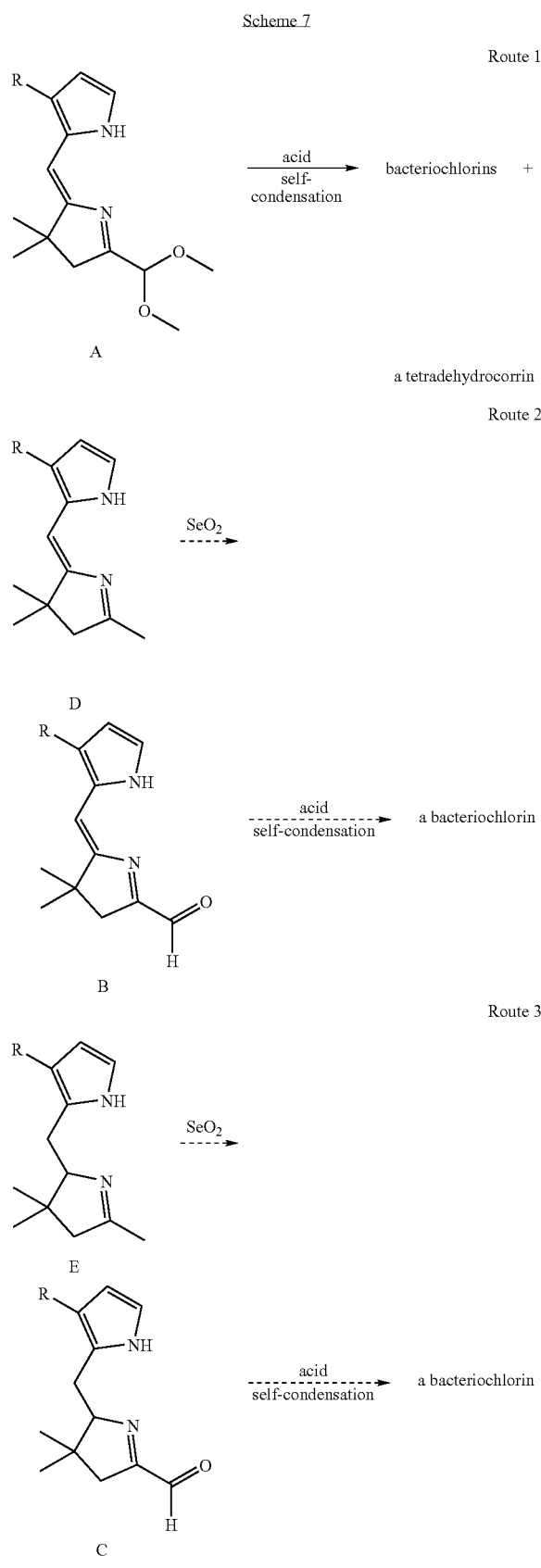

Scheme 7

2. Synthesis of Dihydrodipyrrin-Aldehyde (6). The synthesis of β-substituted dihydrodipyrrin 5 was initiated in a manner analogous to that of previous dihydrodipyrrins (Balasubramanian, T. et al., *J. Org. Chem.* 2000, 65, 7919-7929). Treatment of nitroethyl pyrrole 3 with mesityl oxide containing DBU gave γ-nitrohexanone 4 in 74% yield via Michael addition, as reported recently (Ptaszek, M. et al., *Org. Process Res. Dev.* 2005, in press). Subsequent treatment of 4 with NaOMe followed by a buffered TiCl₃ solution afforded dihydrodiyrrin 5 as a yellow solid in 25% yield. Oxidation of dihydrodipyrrin 5 with SeO₂ gave the corresponding dihydrodipyrrin-aldehyde 6 in 47% yield (Scheme 8). The low yield of the oxidation is attributed to the instability of the aldehyde 6. On the other hand, all attempts to carry out a similar oxidation of tetrahydrodipyrrin 2→C were unsuccessful.

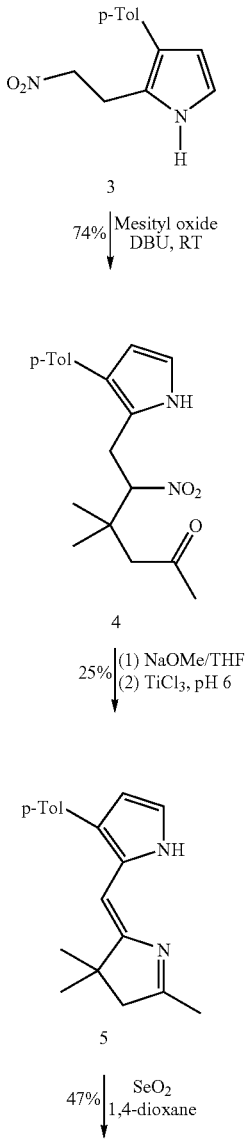

Scheme 8

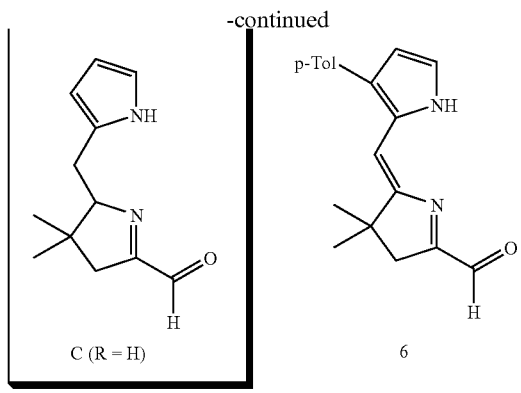

3. Effect of Reactant and Acid Concentrations. For immediate comparison of the self-condensation between the dihydrodipyrrin-acetal and the dihydrodipyrrin-aldehyde, microscale experiments were performed under four different acid concentrations. The concentration of dihydrodipyrrin-aldehyde 6 was 4.7 mM and the concentration of $BF_3 \cdot OEt_2$ varied from 0.47 to 47 mM. Each reaction was monitored over time (18 h). Two bacteriochlorins (H-BC and an unidentified-BC, though expected to be a hydroxybacteriochlorin or a oxo-bacteriochlorin) and a tetradehydrocorrin-aldehyde (TDC-CHO) were detected by absorption spectroscopy and LD-MS (Scheme 9). The collected data for H-BC were consistent with the same bacteriochlorin obtained from the corresponding acetal. LD-MS analysis of TDC-CHO gave a molecule ion peak (m/z=566.2) consistent with the proposed structure; moreover, the absorption spectrum was quite similar with that of TDC (not shown).

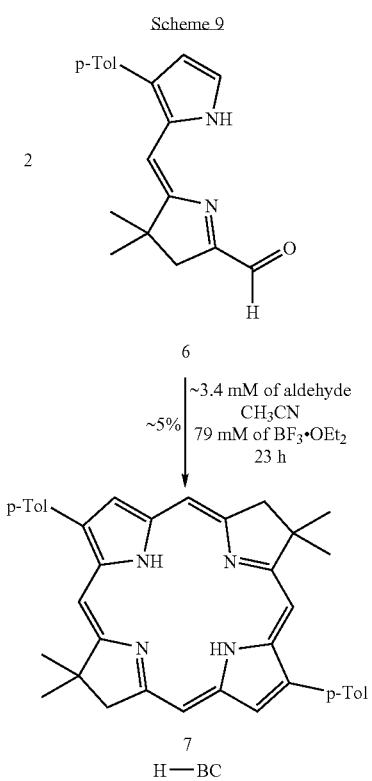

The total yield of bacteriochlorins (but not TDC-CHO) was determined spectroscopically from the crude mixture. Each reaction mixture was then separated chromatographically to determine the isolated yield of the tetradehydrocorrin-aldehyde TDC-CHO (Table 1). The highest spectroscopic yield of the bacteriochlorins was 11% at 47 mM of $BF_3 \cdot OEt_2$ (entry 4). It is noteworthy that the yield of the sum of the bacteriochlorins (entry 4) decreased slowly as the reaction proceeded. The highest yield of TDC-CHO (~4%) was obtained at 2.3 mM of $BF_3 \cdot OEt_2$ (entry 2). The yield of TDC was highest at relatively low acid concentration and was not observed at the highest acid concentration (47 mM).

TABLE 1

Spectroscopic Yields of Hydroporphyrins from Microscale Reactions[a]

| Entry | [6], mM | [$BF_3 \cdot OEt_2$], mM | Yield (Sum of H-BC and an unidentified BC) | TDC-CHO yield[d] |
|---|---|---|---|---|
| 1[b] | 4.7 | 0.47 | 0.2%[c] (5 h)[e] | 1% (18 h) |
| 2[b] | 4.7 | 2.3 | 0.7%[c] (1 h)[e] | 4% (18 h) |
| 3[b] | 4.7 | 4.7 | 0.8%[c] (5 h)[e] | 1% (18 h) |
| 4[b] | 4.7 | 47 | 11%[c] (1 h)[e] | — |

[a]Spectroscopic yields were determined assuming $\epsilon_{Qy}$ = 120,000 $M^{-1}$ $cm^{-1}$ for bacteriochlorins and $\epsilon_{363\,nm}$ = 24,000 $M^{-1} cm^{-1}$.
[b]The reaction was performed using 5.1 μmol of 6.
[c]Highest yield was obtained from crude mixture.
[d]Yield was obtained from isolated fraction.
[e]The data points were taken at 1, 5, and 18 h and the reaction time was taken at highest yield.

4. Synthesis of a Bacteriochlorin (H-BC). The reaction was designed to favor H-BC. The reaction conditions employed for the self-condensation of dihydrodipyrrin-aldehyde 6 were similar to those from the previous condensation of dihydrodipyrrin-acetal 1. The conditions entailed ~3.7 mM of aldehyde 6 in $CH_3CN$ containing 79 mM of $BF_3 \cdot OEt_2$ at room temperature. Samples were removed (50 μL) three times (0.5, 2, 17 h), neutralized with TEA, and examined by absorption spectroscopy. Yields were calculated on the basis that the bacteriochlorin has $\epsilon_{Qy}$=130,000 $M^{-1}$ $cm^{-1}$. The spectroscopic yields of the bacteriochlorin in the crude mixture were ~3% (0.5 h), ~6% (2 h), and ~6% (17 h) respectively. The isolated yield of H-BC was ~5% (Scheme 9).

Experimental Section

General. $^1H$ NMR (400 MHz) spectra were collected at room temperature in $CDCl_3$. Column chromatography was performed with flash silica or alumina (80-200 mesh). Bacteriochlorin was analyzed in neat form by laser desorption mass spectrometry (LD-MS) in the absence of a matrix. Compounds 1 (Taniguchi, M. et al., J. Org Chem. 2001, 66, 7342-7354) and 3 (Kim, H.-J.; Lindsey, J. S. J. Org. Chem. 2005, 70, 5475-5486) were prepared as described in literature.

6-[3-(4-Methylphenyl)pyrrol-2-yl]-4,4-dimethyl-5-nitro-2-hexanone (4). Following a standard procedure (Ptaszek et al., supra), a mixture of 3 (460 mg, 2.00 mmol) and mesityl oxide (458 μL, 4.00 mmol) in $CH_3CN$ (4.0 mL) was treated with DBU (897 μL, 6.00 mmol). The reaction mixture was stirred for 24 h at room temperature, diluted with ethyl acetate (15.0 mL) and washed with water and brine. The organic layer was dried ($Na_2SO_4$) and concentrated. Excess mesityl oxide was removed under high vacuum. The resulting oil was chromatographed [ethyl acetate/hexanes (1:2)] to afford a light brown oil (486 mg, 74%): $^1$H NMR δ 1.08 (s, 3H), 1.19 (s, 3H), 2.10 (s, 3H), 2.37 (s, 3H), 2.37, 2.55 (AB, $^2$J=17.6 Hz, 2H), 3.21 (ABX, $^3$J=2.6 Hz, $^2$J=15.6 Hz, 1H), 3.38 (ABX, $^3$J=11.6 Hz, $^2$J=15.6 Hz, 1H), 5.18 (ABX, $^3$J=2.6 Hz, $^3$J=11.6 Hz, 1H), 6.22-6.24 (m, 1H), 6.67-6.69 (m, 1H), 7.20 (d, J=8.0 Hz, 2H), 7.24 (d, J=8.0 Hz, 2H), 8.05-8.20 (br, 1H).

1,3,3-Trimethyl-7-(4-methylphenyl)-2,3-dihydrodipyrrin (5). Following a standard procedure (see, e.g., Strachan, J.-P. et al., *J. Org. Chem.* 2000, 65, 3160-3172; Strachan, J.-P. et al., *J. Org. Chem.* 2001, 66, 642), a solution of 4 (256 mg, 0.780 mmol) in anhydrous THF (7.8 mL) under argon was treated with NaOMe (210 mg, 3.90 mmol). The mixture was argon bubbled for 10 min and was stirred for 1 h at room temperature (first flask). In a second flask, TiCl$_3$ [8.6 wt % TiCl$_3$ in 28 wt % HCl (d=1.2), 5.83 mL, 3.90 mmol, 5.0 mol equiv] and H$_2$O (31 mL) were combined. The solution was argon bubbled for 10 min. NH$_4$OAc (22.9 g, 297 mmol) was slowly added to buffer the solution to pH 6.0; and then THF (2.2 mL) was added under argon bubbling (~20 min). The solution in the first flask containing the nitronate anion of 4 was transferred via a cannula to the buffered TiCl$_3$ solution in the second flask. The resulting mixture was stirred at room temperature for 6 h under argon. Then the mixture was slowly poured to a stirring solution of saturated aqueous NaHCO$_3$ (120 mL) and ethyl acetate (40 mL). After 10 min, the mixture was extracted with ethyl acetate. The combined organic layers were washed with water and then dried (NaSO$_4$). The solvent was removed under reduced pressure at room temperature. The crude product was passed through a short column [alumina, hexanes/ethyl acetate (2:1)] to afford a yellow solid (55 mg, 25%): $^1$H NMR δ 1.18 (s, 6H), 2.21 (s, 3H), 2.38 (s, 3H), 2.51 (s, 2H), 5.97 (s, 1H), 6.27-6.28 (m, 1H), 6.84-6.86 (m, 1H), 7.21 (d, J=8.0 Hz, 2H), 7.36 (d, J=8.0 Hz, 2H), 10.99-11.10 (br, 1H).

1-Formyl-3,3-dimethyl-7-(4-methylphenyl)-2,3-dihydrodipyrrin (6). Following a general procedure (Jacobi, P. A. et al.,. *Org. Lett.* 2001, 3, 831-834), a solution of 5 (45 mg, 0.16 mmol) in 1,4-dioxane (3.2 mL) was treated with SeO$_2$ (27 mg, 0.24 mmol) under argon. The mixture was stirred for 1.5 h at room temperature. The reaction mixture was treated with saturated NaHCO$_3$ (4.0 mL) and extracted with ethyl acetate. The organic extract was washed with water, dried (Na$_2$SO$_4$), and chromatographed [silica, ethyl acetate/hexanes (1:3)] to give a dark orange solid (22 mg, 47%): $^1$H NMR δ 1.22 (s, 6H), 2.41 (s, 3H), 2.72 (s, 2H), 6.34-6.35 (m, 1H), 6.38 (s, 1H), 7.00-7.02 (m, 1H), 7.25 (d, J=8.0 Hz, 2H), 7.35 (d, J=8.0 Hz, 2H), 10.0 (s, 1H), 10.71-10.82 (br, 1H). FAB-MS obsd 293.1654, calcd 293.1654 [(M+H)$^+$, M=C$_{19}$H$_{20}$N$_2$O].

8,8,18,18-Tetramethyl-2,12-bis(4-methylphenyl)bacteriochlorin (7, H-BC).

A solution of 6 (~1 mg, 3.4 µmol) in CH$_3$CN (1.0 mL) was treated with BF$_3$.OEt$_2$ (10 µL, 79 µmol). The reaction mixture was stirred at room temperature without deaeration for 23 h. TEA (12 µL, 86 µmol) was added to the reaction mixture. The reaction mixture was concentrated and the residue was chromatographed [silica, CH$_2$Cl$_2$/hexanes (1:1)] to give a green solid (H-BC, ~0.05 mg, 5%). The product co-chromatographed [silica, hexanes/CH$_2$Cl$_2$ (1:1), R$_f$=0.77] with an authentic sample of H-BC prepared from the dihydrodipyrrin-acetal 1. The absorption spectrum and LD-MS data were consistent with previously reported values: λ$_{abs}$(CH$_2$Cl$_2$)/nm 350, 373, 498, 737; LD-MS obsd 549.5, calcd 550.31 (C$_{38}$H$_{38}$N$_4$).

The foregoing is illustrative of the present invention, and is not to be construed as limiting thereof. The invention is defined by the following claims, with equivalents of the claims to be included therein.

What is claimed is:

1. A method of making a compound of Formula I:

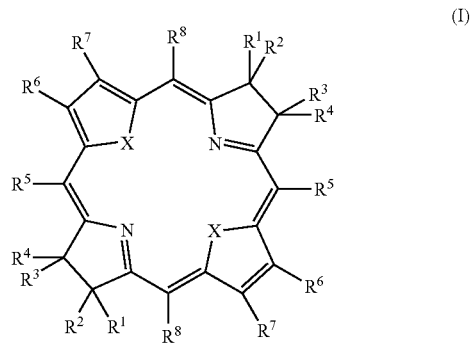

(I)

wherein:

X is NH;

R$^1$ and R$^2$ are each independently selected from the group consisting of H, alkyl, aryl, alkoxy, halo, mercapto, cyano, hydroxyl, nitro, acyl, alkylthio, alkylamino, acyloxy, and —C(O)NR$_a$R$_b$ where R$_a$ and R$_b$ are each independently selected from the group consisting of alkyl, cycloalkyl, alkenyl, alkynyl and aryl;

R$^3$ and R$^4$ are each independently selected from the group consisting of alkyl, cycloalkyl, aryl, and arylalky;

R$^5$ is selected from the group consisting of H, alkyl, alkenyl, alkynyl, cycloalkyl, aryl, arylalkyl, arylalkenyl, arylalkynyl, alkoxy, halo, cyano, nitro, acyl, alkylthio, alkylamino, arylalkylamino, disubstituted amino, acylamino, acyloxy, and —C(O)NR$_a$R$_b$ where R$_a$ and R$_b$ are each independently selected from the group consisting of alkyl, cycloalkyl, alkenyl, alkynyl and aryl;

R$^6$ and R$^7$ are each independently selected from the group consisting of H, alkyl, alkenyl, alkynyl, cycloalkyl, aryl, arylalkyl, arylalkenyl, arylalkynyl, halo, cyano, nitro, acyl, alkoxy, alkylthio, alkylamino, arylalkylamino, disubstituted amino, acylamino, acyloxy, —C(O)NR$_a$R$_b$ where R$_a$ and R$_b$ are each independently selected from the group consisting of alkyl, cycloalkyl, alkenyl, alkynyl and aryl, —C(O)OR$_c$ where R$_c$ is selected from the group consisting of alkyl, cycloalkyl, alkenyl, alkynyl and aryl, and C(O)OH; and R$^8$ is selected from the group consisting of H, alkyl, alkenyl, alkynyl, cycloalkyl, aryl, arylalkyl, arylalkenyl, arylalkynyl, halo, cyano, nitro, acyl, alkoxy, alkylthio, alkylamino, arylalkylamino, disubstituted amino, acylamino, acyloxy, and —C(O)NR$_a$R$_b$ where R$_a$ and R$_b$ are each independently selected from the group consisting of alkyl, cycloalkyl, alkenyl, alkynyl and aryl;

said method comprising condensing a pair of compounds of Formula II:

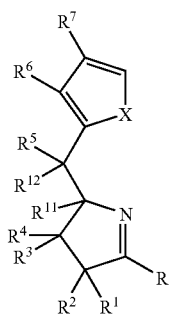

in an organic solvent in the presence of an acid to produce the compound of Formula I, wherein:
R is —C(OR$_d$)(OR$_e$)H or —C(O)H, where R$_d$ and R$_e$ are each independently selected from the group consisting of alkyl, aryl, and alkylaryl, or where R$_d$ and R$_e$ together form a group —R"— where R" is an alkylene;
X and R$^1$ to R$^7$ are as given above; and
R$^{11}$ and R$^{12}$ are each H; or R$^{11}$ and R$^{12}$ together form a covalent bond.

2. The method of claim 1, wherein said compound of Formula II is a compound of Formula IIa:

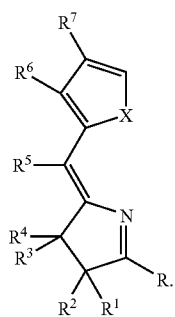

3. The method of claim 1, wherein said compound of Formula II is a compound of Formula IIb:

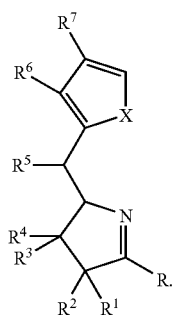

4. The method of claim 1, wherein R is —C(OR$_d$)(OR$_e$)H.

5. The method of claim 1, wherein R is —C(O)H.

6. A method of making a compound of Formula I:

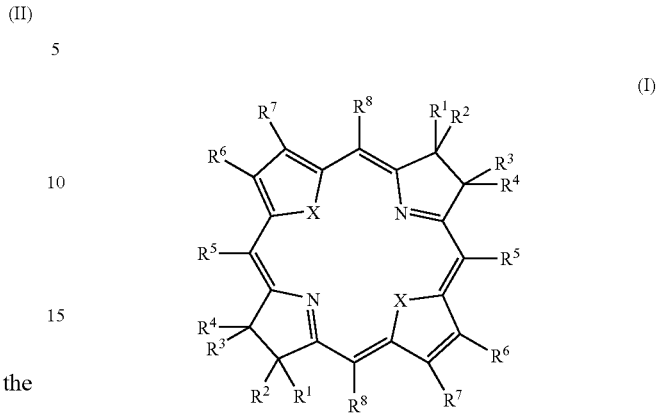

wherein:
X is NH;
R$^1$, R$^2$, R$^5$, R$^7$ and R$^8$ are each H;
R$^3$ and R$^4$ are each methyl; and
R$^6$ is p-tolyl;
said method comprising condensing a pair of compounds of Formula II:

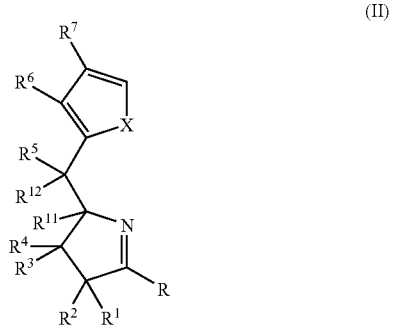

in an organic solvent in the presence of an acid to produce the compound of Formula I, wherein:
R is —C(OR$_d$)(OR$_e$)H or —C(O)H, where R$_d$ and R$_e$ are independently selected from the group consisting of alkyl, aryl, and alkylaryl, or where R$_d$ and R$_e$ together form a group —R"— where R" is an alkylene; and
R$^{11}$ and R$^{12}$ are each H; or R$^{11}$ and R$^{12}$ together form a covalent bond.

* * * * *